(12) United States Patent
Zhou et al.

(10) Patent No.: US 7,728,978 B2
(45) Date of Patent: Jun. 1, 2010

(54) DETECTION OF MOISTURE IN REFRIGERANTS

(75) Inventors: Xin Zhou, Rancho Cucamonga, CA (US); Xiang Liu, Phoenix, AZ (US); Gregory M. Sanger, Chico, CA (US)

(73) Assignee: SpectraSensors, Inc., Rancho Cucamonga ( * ) Notice: Subject to any disclaimer, the term of this patent is extended or adjusted under 35 U.S.C. 154(b) by 356 days.

(21) Appl. No.: 11/873,723

(22) Filed: Oct. 17, 2007

(65) Prior Publication Data

US 2008/0092648 A1    Apr. 24, 2008

Related U.S. Application Data

(60) Provisional application No. 60/853,313, filed on Oct. 18, 2006.

(51) Int. Cl.
*G01N 21/00* (2006.01)
*G01N 21/37* (2006.01)

(52) U.S. Cl. .......... 356/437; 356/436; 250/343
(58) Field of Classification Search ......... 356/432–444; 250/338.5, 343, 339.13, 38.5; 73/335.01, 73/335.04, 29.05
See application file for complete search history.

(56) References Cited

U.S. PATENT DOCUMENTS

| | | | | |
|---|---|---|---|---|
| 5,528,040 A | * | 6/1996 | Lehmann | 250/343 |
| 5,777,735 A | * | 7/1998 | Reagen | 356/451 |
| 6,150,661 A | * | 11/2000 | McCaul et al. | 250/343 |
| 6,657,198 B1 | * | 12/2003 | May | 250/339.13 |
| 7,132,661 B2 | * | 11/2006 | May | 250/343 |
| 7,166,843 B2 | * | 1/2007 | May | 250/343 |
| 7,339,168 B2 | * | 3/2008 | May | 250/338.5 |
| 2004/0079887 A1 | | 4/2004 | May | |
| 2008/0123712 A1 | * | 5/2008 | Zhou et al. | 372/55 |

FOREIGN PATENT DOCUMENTS

WO    WO 03/100393 A1    12/2003

OTHER PUBLICATIONS

Edwards, C.S, et al., "A tunable diode laser absorption spectrum for moisture measurements in the low parts in $10^9$ range," *Meas. Sci. Technol.* 12 (2001) 1214-1218.

(Continued)

*Primary Examiner*—Sang Nguyen
(74) *Attorney, Agent, or Firm*—Mintz, Levin, Cohn, Ferris, Glovsky & Popeo, P.C.

(57) ABSTRACT

Moisture can be detected in a refrigerant background such as HFC (Hydrofluorocarbon) HFC-134A and HFC-152A and exampled by HFC-23, HFC-32, HFC-143A, HFC-125, HFC-245FA, HFC-227EA, and the like. The system can include a light source operating at any one of several wavelengths within the water absorption bands at wavelengths such as 1.4, 1.9 and 2.7 μm and a detector that measures the transmitted light intensity through the HFC samples. In one variation, the light source is a tunable diode laser and the moisture level is determined by direct absorption and harmonic spectroscopy. Related techniques, apparatus, systems, and articles are also described.

25 Claims, 10 Drawing Sheets

OTHER PUBLICATIONS

Paige, Mark E., "Commercial Gas Sensing with Vertical Cavity Lasers," *Advanced Semiconductor Lasers and their Applications Conference, 1999 Technical Digest*.

Zhou, X., et al., "Development of a fast temperature sensor for combustion gases using a single tunable diode laser," *Appl. Phys.* B 81, 711-722 (2005).

Wysocki, G., et al., "Spectroscopic trace-gas sensor with rapidly scanned wavelengths of a pulsed quantum cascade laser for in situ NO monitoring of industrial exhaust systems," *Appl. Phys.* B 80, 617-625 (2005).

* cited by examiner

DETECTION OF MOISTURE IN REFRIGERANTS

RELATED APPLICATIONS

The present patent application claims priority under 35 U.S.C. §119 to U.S. Provisional Patent Application Ser. No. 60/853,313, filed on Oct. 18, 2006, and entitled "Detection of Moisture in Refrigerants", the entire disclosure of which is incorporated by reference herein.

TECHNICAL FIELD

The subject matter described herein relates to the detection of moisture in refrigerants.

BACKGROUND

There are approximately 336 refrigerants used in a myriad of applications worldwide. Most are variations of the $C_N F_M H_X Cl_Y$ molecule with a small number having trailing Br and O atoms attached. Of these, the most common and widely used are hydrofluorocarbons (HFCs) as represented by HFC-134A, HFC-152A, HFC-23, HFC-32, HFC-143A, HFC-125, HFC-245FA, HFC-227EA as their contribution to atmospheric ozone depletion is much smaller than most others.

Common HFCs such as HFC 134A, 407C, 410A and 152A are finding an increasing variety of applications related to comfort cooling chillers (residential, industrial or automotive), commercial refrigeration, and industrial process refrigeration where such refrigerants are required. This increased adoption is due to the fact that the more commonly used freons until recently contain chlorofluorocarbons (CFCs) or hydrochlorofluorocarbons (HCFCs) which are being phased out in the United States and internationally due to their adverse effect (ozone depletion) on the earth's atmospheric environment. Therefore, HFCs have become much more prevalent in the applications mentioned above. Under section 608 of the Clean Air Act, it has been illegal since Nov. 15, 1995, to knowingly vent substitutes for CFC and HCFC refrigerants during the maintenance, service, repair and disposal of air-conditioning and refrigeration equipment. Therefore, though the HFCs are allowed as refrigerants, they cannot be vented to atmosphere either so their careful treatment is important.

The moisture content of these refrigerants is often critical to their application in such chiller applications as levels of frost and/or ice can form in expander valves and chambers should the moisture content be too high. Such freezing can seriously degrade or even destroy the process or the product in which they are employed and cause problems for maintenance or perhaps even unwanted venting prohibited by the above statutes. As a result, both producers and users have a strong need to determine the amount of moisture in the HFC they use or sell. Gas producers need to understand the trace moisture content of their gases so that they can assure themselves that products contain only the miniscule amounts of moisture they claim. Users need to measure moisture in these same gases to assure themselves that the stock gases being used do not adversely affect the product into which they are introduced.

Conventional techniques for measuring moisture in HFCs have significant disadvantages such as maintenance and calibration issues in the field that can be costly and time consuming to address.

Some conventional sensors for detecting moisture in refrigerants employ chilled sensors. With such devices, when gas flows over a chilled surface (such as a mirror) the moisture will condense on it—the exact temperature at which this condensation begins is the dew point. The temperature of the mirror is reduced from high to low (so that it passes through the dew point temperature), and the temperature is read exactly when the dew is observed. By obtaining the dew point temperature, one can calculate the moisture content in the gas. The mirror temperature is controlled by the flow of a refrigerant over the mirror or by using a thermoelectric cooler. The detection of condensation on the mirror can be done by eye or by optical means. For example, a light source can be reflected off the mirror into a detector and condensation detected by changes in light reflected from the mirror. The observation can also be done by eye; however the exact point at which condensation begins is not visible to the eye. Also, because the temperature is passing through the dew point rather than stopping exactly at the dew point, the measurement tends to be high and will have a high standard deviation. Additionally, the condensation of moisture can be confused with condensation of other condensable gases such as heavy hydrocarbons, alcohol, glycol or the refrigerant itself. Automated on-line systems are not able to make these distinctions and manual systems must be used only by highly skilled operators.

Other conventional sensors for detecting moisture in natural gas utilize an electrolytic sensor that includes two closely spaced, parallel windings coated with a thin film of Phosphorous Pentoxide ($P_2O_5$). As this coating absorbs incoming water vapor, an electrical potential is applied to the windings that electrolyzes the water to hydrogen and oxygen. The current consumed by the electrolysis determines the mass of water vapor entering the sensor. The flow rate and pressure of the incoming sample must be controlled precisely to maintain a standard sample mass flow rate into the sensor. With such a sensor, contamination from oils, liquids, glycols or the refrigerant itself on the windings will cause drift in the readings and damage to the sensor. The sensor cannot react to sudden changes in moisture, i.e. the reaction on the windings' surfaces takes some time to equalize. Large amounts of or large upward changes to the amount of water in the sample gas (called slugs) will wet the surface and can require tens of minutes or hours to "dry-down".

Instruments utilizing a piezoelectric adsorption sensor that operate by comparing changes in frequency of hydroscopically coated quartz oscillators can also be used to detect moisture in refrigerants. As the mass of the crystal changes due to adsorption of water vapor, the resonant frequency of the quartz crystal changes. The sensor is a relative measurement so an integrated calibration system with desiccant dryers, permeation tubes and sample line switching is used to correlate the system on a frequent basis. Interference from glycol, methanol, and damage from hydrogen sulfide or other sulfides or other contaminants result in readings that cannot be relied on. Such a sensor requires a calibration system which is often imprecise and adds to the cost and mechanical complexity of a system. In addition, the labor for frequent replacement of desiccant dryers, permeation components, and the sensor heads greatly increase the operational costs. Moreover, slugs of water render the system nonfunctional for long periods of time as the sensor head has to "dry-down".

An oxide sensor that is made up of an inert substrate material and two conductive layers. The sandwiched inert material is sensitive to humidity and may be used to detect moisture in refrigerants as its dielectric properties change with increased absorbance of moisture. With such a sensor, moisture molecules pass thru the pores on the surface layer and cause a change to a physical property of the layer beneath it. An example is an aluminum oxide sensor which has two metal layers forming the electrodes of a capacitor. The number of water molecules adsorbed will cause a change in the dielectric constant of the sensor. The sensor capacitance is correlated to the water concentration. Another similar sensor concept is a silicon oxide sensor. It is an optical device that changes it refractive index as water is absorbed into the sensitive layer. When light is reflected through the substrate, a wavelength shift can be detected on the output which can be precisely correlated to the moisture concentration. Fiber optic connector may be used to separate the sensor bead and the electronics.

With such a sensor, water molecules take time to enter and exit the pores so some wet-up and dry down delays will be observed, especially after a slug. Contaminants and corrosives may damage and clog the pores causing a "drift" in the calibration, but the sensor heads can be refurbished or replaced and will perform better in very clean gas streams. As with the piezoelectric and electrolytic sensors, the sensor is susceptible to interference from glycol and methanol, the calibration will drift as the sensor's surface becomes inactive due to damage or blockage, so the calibration is reliable only at the beginning of the sensor's life.

Optical sensors have also been developed for use in measuring gases within HFCs. Some implementations measure gases in refrigerants by determining the broadband spectrum of the refrigerant in the absence of a sensing reagent using a broadband detector and a monochrometer or some such selectable monochromatic light source and comparing the spectrum into that of various types of refrigerants. The refrigerant spectrum that matches the measured spectrum is the refrigerant present. With such a sensor, concentration of the refrigerant or the included trace gases can be determined, however, the lower detection limit of this type of device is greater than is needed in many applications.

Other optical sensors measure a continuous spectrum using broadband light that is directed to a series of detectors sensitive to a variety of pre-selected infrared light frequencies. Such frequencies are selected such that when a certain combination of relative absorption is seen, the refrigerant or included trace gas can be identified. Such an arrangement also has a higher detection limit than is desired for many applications. Moreover, only small segments of the broadband spectrum can be used for measurement, thereby leading to false readings and considerable measurement complexity if there is more than one gas type present, particularly when the absorption bands fall in the same place (i.e.—interferences).

SUMMARY

Techniques and systems are described that can detect and quantify the moisture content in refrigerants, for example, HFCs. Sample HFCs include HFC-134A, HFC-152A, HFC-23, HFC-32, HFC-143A, HFC-125, HFC-245FA, and HFC-227EA.

In one aspect, trace amounts of water vapor in a refrigerant gas are determined by directing a beam of light at a selected wavelength through a refrigerant gas comprising water vapor at low concentrations. The selected wavelength can coincide with a water vapor absorption feature that is resolvable from an absorption background of the refrigerant gas. Absorption at the selected wavelength in the refrigerant gas over a path length can be quantified to allow a determination of water vapor concentration in the refrigerant gas based on the quantified absorption. This determined, water vapor concentration can then be promoted.

The promoting can comprise, for example, one or more of displaying, transmitting, or storing the determined water vapor concentration.

The gas mixture can be contained within a sample cell that provides the path length.

The absorption at the selected wavelength can be quantified with a photodetector that provides an electronic output signal to a microprocessor where the concentration can be computed.

In some implementations, more than one light source is utilized, or a tunable light source is utilized. In such variations, light can be generated with a range of wavelengths that include the selected wavelength, and the generated light can be tuned across such range. An AC signal from a photodetector that the light beam impinges upon after traversing the refrigerant gas can be converted to an absorption signal by amplifying, demodulating and digitizing the AC signal. This signal can be analyzed by a microprocessor to determine the water vapor concentration.

The absorption at the selected wavelength can be quantified using direct absorption, harmonic, photoacoustic, cavity ringdown, integrated cavity output, or cavity enhanced spectroscopic techniques.

The water vapor concentration can be less than or equal to approximately 1 ppm and/or less than or equal to approximately $10^{-4}$%.

The selected wavelength can correspond to a water absorption line at or adjacent to a wavelength selected from a group comprising: 1359.5 nm, 1361.7 nm, 1368.6 nm, 1371.0 nm, 1392.0 nm, 1836.3 nm, 1840.0 nm, 1842.1 nm, 1847.1 nm, 1854.0 nm, 1856.7 nm, 1859.8 nm, 1877.1 nm, 1890.3 nm, 1899.7 nm, 1903.0 nm, 1905.4 nm, 2573.6 nm, 2583.9 nm, 2596.0 nm, 2605.6 nm, 2620.5 nm, 2626.7 nm, 2630.6 nm, 2665.1 nm, 2676.0 nm, 2711.2 nm, 2724.2 nm, 2735.0 nm, and 2740.0 nm.

The refrigerant gas can comprises a hydrofluorocarbon, such as, one or more of HFC-134A, HFC-152A, HFC-23, HFC-32, HFC-143A, HFC-125, HFC-245FA, and HFC-227EA.

In another aspect, an apparatus comprises a laser light source that emits a light beam comprising a selected wavelength that coincides with a water vapor absorption feature that is resolvable from a gas absorption background of a refrigerant gas, a sample cell providing a path length to contain the refrigerant gas, a photodetector positioned to quantify an intensity of light traversing the path length and to output a data signal based on the quantified intensity, and a microprocessor configured to receive and interpret the signal from the photodetector and to determine the water vapor concentration in the refrigerant gas based on the direct current data signal.

Such techniques and systems may, for example, use absorption spectroscopy in which a light source emits light through a sample of refrigerant gas which is subsequently detected by a detector. The light source may be any of a variety of light sources, including, without limitation, a tunable diode laser, a color center laser, a quantum cascade laser, a VCSEL, a HCSEL, a DFB, and any other light source having a sufficiently narrow line width at or around a wavelength of interest to conduct absorption spectroscopy (at or in relation to one or more absorption lines). The detector may be, for example, an InAs or an InGaAs photodiode.

Sample wavelength ranges include absorption lines at or near 1.4 µm, 1.9 µm, 2.7 µm (see Table 1). However, it will be appreciated that other wavelength ranges may be utilized provided that water molecules absorb light at a substantially greater level than do HFC molecules.

In some variations, housings may be used to increase optical path length such as a Herriott cell, a White cell, an off-axis resonating cavity, a cavity ring down cell, an astigmatic cell and the like in which opposing mirrors reflect light introduced into such sample cells and is subsequently detected (after two or more passes) by one or more detectors.

In another aspect, a method for determining the level of moisture in HFCs is described that provides a light source emitting light substantially at a wavelength of interest, positions a detector opposite the light source to detect the level of the emitted light after passing through a sample gas, and determines the moisture level based on the level of light detected by the detector. In such a method, the gas can be obtained by a probe tap from a HFC pipeline, storage tank or expander tank and directed into a shelter or other location where an analyzer designed to perform such a method is housed. The gas can also be obtained from other sources in which it useful to determine moisture content in refrigerants. It is also possible that the analyzer can be configured to be portable allowing for measurements in remote or field locations where the necessary utilities may not be available.

The details of one or more variations of the subject matter described herein are set forth in the accompanying drawings and the description below. Other features and advantages of the subject matter described herein will be apparent from the description and drawings, and from the claim.

DETAILED DESCRIPTION

Figure 1:
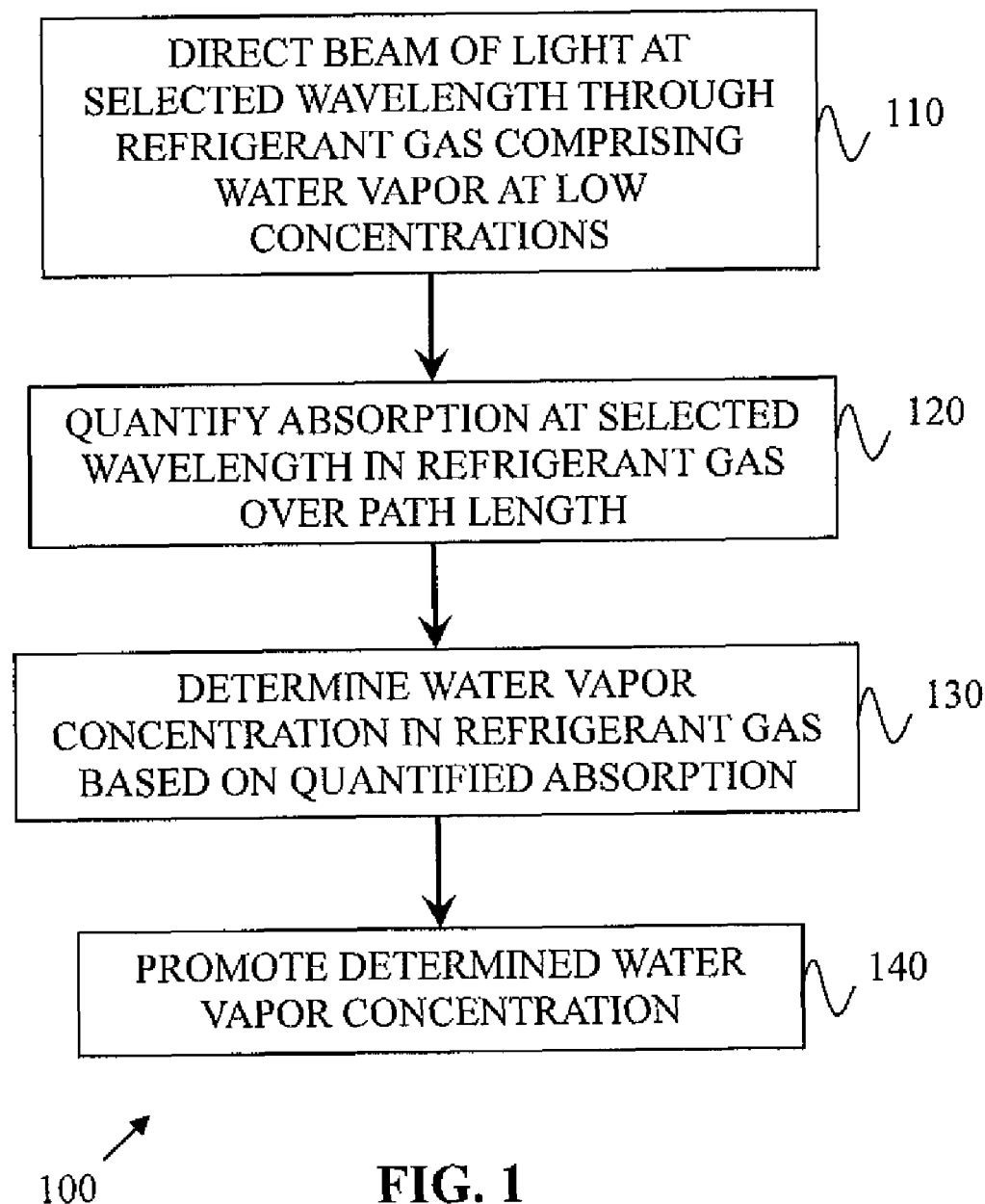
FIG. 1 is a process flow diagram illustrating a method for detecting moisture within refrigerants.

The subject matter described herein utilizes absorption spectroscopy to measure the concentration of gases. With such a spectroscopic technique, a light beam is passed through a gas sample and detected by a photodetector. The light source can be a conventional hot filament, a glow bar, an LED, a laser, or any suitable light emitter in the wavelength region of interest. By monitoring the amount of light absorbed by the sample, at specific wavelengths, the concentration of the target gas can be accurately determined. The longer the path of the light that travels through the sample gas of interest, the more light is absorbed. As such, the sensitivity of the spectrometer can be varied by the total pathlength of the sample cell.

Near infrared radiation generally lacks sufficient photon energy to induce absorption by electronic transitions such as those induced by ultraviolet radiation. Therefore, IR absorption is restricted to compounds with small energy differences in the possible vibrational and rotational states of the molecules. For a molecule to absorb IR radiation, vibrations or rotations within a molecule must cause a net change in the dipole moment of the molecule. The alternating electrical field of the radiation interacts with fluctuations in the dipole moment of the molecule. The energy of the incident light radiation is $$E = h\nu \quad (1)$$

where E is the photon energy, h is Planck's constant and ν is the frequency of the light. If E matches the energy necessary to excite a vibrational mode of a molecule, then radiation will be absorbed causing a change in the amplitude of this molecular vibration. The three main types of molecular motion, which includes relative motion between atoms making up the molecule, involve torsion, stretching and vibration of interatomic bonds.

Stretching and torsional transitions require moderate energies and are therefore quite useful to IR absorption spectroscopy. In stretching transitions for instance, the inter-atomic distance changes along bond axes, and the resultant absorbance of IR by gas-phase molecules yield line spectra sufficiently spaced apart to allow detection. In liquids or solids, these lines broaden into a continuum due to molecular collisions and other interactions such that they cannot be measured by IR absorption spectroscopy.

The relative positions of atoms in molecules are not fixed, but are rather subject to a number of different vibrations relative to other atoms in the molecule. A specific molecular motion requires a corresponding quantum of activating photon energy. Therefore, an incident photon's energy must be of exactly the right wavelength to be absorbed into the molecule. Thus, if a gas containing a molecule that absorbs at a given wavelength λ is illuminated by a beam of light of the same wavelength, some of the incident photons will be absorbed as it passes through the gas. This absorbance $A_{i,\lambda}$ is calculated from the beam power incident on the sample $P_0$ and the beam power passing through the sample P as follows:

$$A_{i,\lambda} = -\ln(P/P_0) \quad (2)$$

In accordance with Beer-Lambert's Law, the absorbance $A_{i,\lambda}$ due to a specific gas-phase compound i at the incident wavelength λ is directly proportional to its concentration $C_i$ in the cell:

$$A_{i,\lambda} = C_i \in_{i,\lambda} L \quad (3)$$

where $\in_{i,\lambda}$ is the extinction coefficient for the compound at the incident wavelength, and L is the path length of the absorption/sample cell.

An analyzer used in connection with the subject matter disclosed here can be used to make water vapor concentration measurements at low levels of water vapor in refrigerant gases. In general, such an analyzer includes a source of incident light, such as a laser, one or more detectors with sensitivity in the wavelength range of the light source, and one or more absorption cells, each arranged such that the gas provides a path length L though which a beam from the light source passes before reaching the detector. Control electronics, such as a microprocessor, and user accessible input/output channels can also be included. The following is a general description of various examples of such devices and their operation.

FIG. 1 is a process flow diagram illustrating a method 100, in which, at 110, a beam of light is directed at a selected wavelength through a refrigerant gas comprising water vapor at low concentrations. The selected wavelength coinciding with a water vapor absorption feature that is resolvable from an absorption background of the refrigerant gas. Absorption at the selected wavelength in the refrigerant gas over a path length can, at 120, be quantified. Based on this quantification, at 130, a water vapor concentration in the refrigerant gas based on the quantified absorption can be determined. Thereafter, at 140, the determined water vapor concentration can be promoted.

In one implementation, a sample of a refrigerant containing water vapor is illuminated by a laser light source that emits light either in a continuous or a pulsed beam. The light source can be a laser such as a tunable diode laser (TDL) or alternatively a fixed wavelength laser light source operating at a specific wavelength chosen to have detectable water vapor absorption without interference from background absorbance by the main component of the gas. The calibration function can be determined based on analysis of one or more samples of gas containing water vapor at known concentrations. The samples are analyzed using the analyzer to be used in the above method. Absorption of light at the selected wavelength is quantified for each sample, and a fitting function is applied to relate water vapor concentration to measured absorption. The calibration function can be a linear relationship or it can alternatively be a more complex mathematical function.

Examples of tunable lasers that can be used are the distributed feedback laser (DFB), the vertical cavity surface emitting laser (VCSEL), and the horizontal cavity surface emitting laser (HCSEL). These lasers can be direct emitters or fiber coupled. Quantum cascade lasers can also be utilized as can other lasers capable of producing a beam of incident light in the desired wavelength range. Additional detail about these types of lasers is available in co-pending U.S. patent application Ser. No. 11/715,599, the disclosure of which is hereby incorporated by reference in its entirety.

Figure 2:
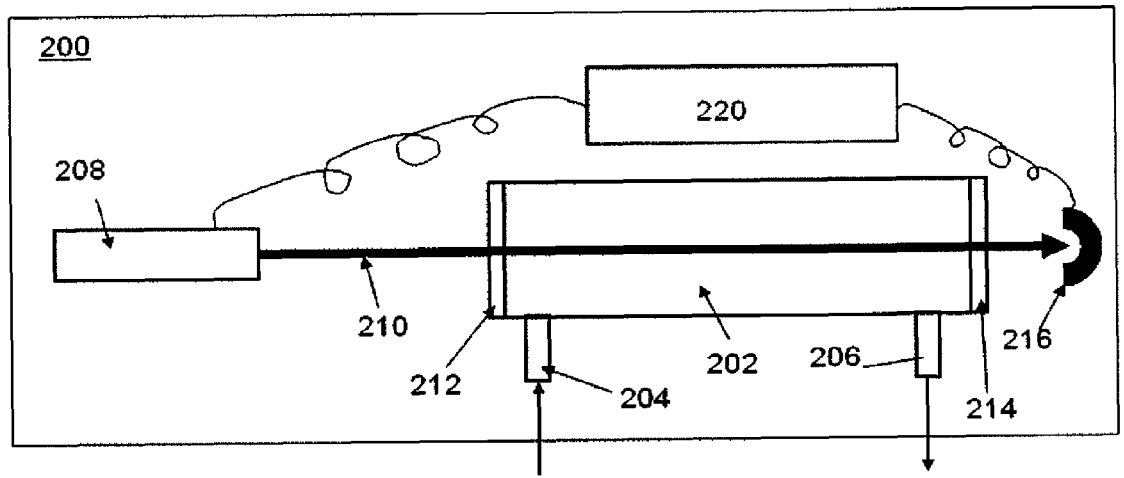
FIG. 2 is a schematic diagram showing an example of an absorption spectrometer.

An illustrative implementation of an analyzer as disclosed herein is depicted schematically in FIG. 2, which shows an analyzer 200 that implements various aspects of the current subject matter. In this implementation, a gas sample is contained within a sample cell 202. The gas sample can be directed into the sample cell 202 via an inlet 204 and flushed from the sample cell 202 via an outlet 206. In some variations, the inlet 204 and the outlet 206 can include valves that can seal the inner volume of the sample cell 202 to obtain a static measurement of a fixed volume of gas. If there are no inlet and outlet valves, or if the inlet and outlet valves are open, the system can be used in a continuous or semi-continuous flow mode, such as for example to continuously or semi-continuously monitor the concentration of a target analyte in a flowing gas stream. For continuous or semi-continuous operation, all or part of a gas stream is directed into the sample cell 202 via the inlet 204 and flushed out of the sample cell 202 via the outlet 206 by the flow of the gas. Flow through the sample cell 202 can be caused by a pressure differential created by a pump or some other mechanism.

A light source 208 that provides light with at least a wavelength where water vapor absorption can be resolved from the gas background absorption generates a continuous or pulsed beam 210 that is directed through the gas volume of the sample cell 202. In the example shown in FIG. 2, the sample cell includes windows 212 and 214 which can be coated to optimize transmittance of the wavelength of interest, allow the light beam 210 to enter and exit the cell. The light beam 210 is directed onto a photodetector or other device for quantifying the intensity of incident light 216 as the light beam exits the sample cell 202. The photodetector 216 is electronically coupled to a control unit 220 that can optionally also be electronically coupled to the light source 208 as shown in FIG. 2. The control unit 220 can include one or more processors coupled to a memory that stores instructions in computer readable code. When executed on the processor or processors, the instructions can implement a method, such as for example that described above, to analyze the absorption at the second or reference wavelength to infer and compensate for the absorption at the first or target wavelength that is due to the background analyte. Once the absorption at the first or target wavelength is so compensated, the control unit 220 can calculate the target analyte concentration.

If the control unit 220 is electronically connected to the light source 208, it can optionally control the light source. For example, if the light source 208 is a tunable diode laser, such as one of those described in U.S. patent application Ser. No. 11/715,599, the control unit can control the scan rate and also interpret the direct voltage measurements by the photodetector 216 to convert them to modulated values. The control unit can also adjust the modulation amplitude as necessary to improve spectral resolution.

Other analyzer configurations besides that shown in FIG. 2 are possible, including but not limited to those described in co-pending U.S. patent application Ser. No. 11/715,599. The sample cell 202 can be a single pass design in which the light beam 210 from the light source 208 passes once through the gas volume of the sample cell 202 before exiting the sample cell 202. In this configuration, the optical path length is effectively the length of the sample cell 202. It is also possible to use one or more mirrors that reflect the light beam 210 such that it passes through the sample volume more than once before exiting the sample cell 202. A Herriott cell (described in full detail in co-pending U.S. patent application Ser. No. 11/715,599), in which the light beam 210 is reflected between two spherical mirrors numerous times to create a very long optical path length, can also be used. The optical path length can be selected based on the strength of the absorption features being used in a measurement and the concentration of the gases being analyzed.

The path length of the sample cell can be varied depending on the strength of the specific absorption line of interest or the magnitude of the difference between the absorption line of interest and interfering absorption lines from other gas species present. A cell of insufficient length can not provide sufficient sensitivity while one of excessive length can absorb the entirety of the incident light such that no measurable signal reaches the detector (a situation called saturation).

In some cases, the water vapor concentration can be very small or not readily distinguishable from other components present in the gas. In such cases, the length of the cell can be increased to increase the sensitivity of the measurement. As equation 3 states, $A_{i,\lambda}$ is directly proportional to the path length L over which the laser beam traverses the gas mixture. Thus, a cell that is twice as long will absorb twice as much light providing that the pressure, temperature and mix of gases present remain the same. Therefore, in some implementations of the analyzers described here, sample cells can be employed having path lengths on the order of many meters or even thousands of meters.

To achieve longer optical path lengths without the use of extremely long sample cells, sample cell configurations within the scope of this disclosure can also include the use of one or more mirrors to reflect the beam such that the beam passes through the sample contained in the sample cell two or more times. In such a multi-pass configuration, the beam can enter and exit the cell through the same window or through different windows. In some implementations, windowless sample cell configurations can be utilized in which, for example, the laser source and/or the photodetector are contained within the sample cell.

Figure 3:
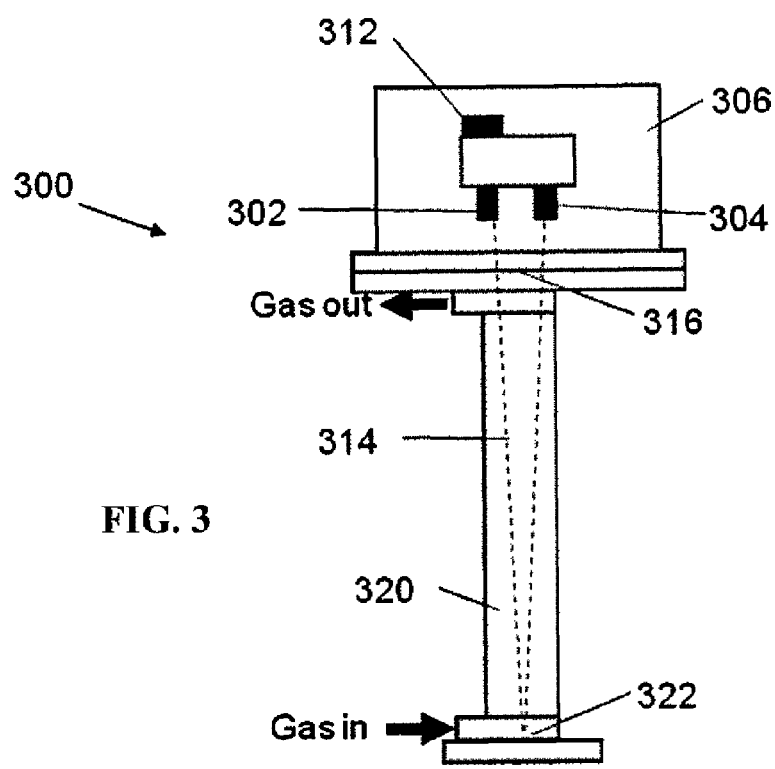
FIG. 3 is a schematic diagram showing an example of a multipass absorption cell.

One example of such a multi-pass sample cell configuration is shown in FIG. 3, which depicts a two-pass absorption cell and laser/detector head 300. A laser 302 and photodetector 304 are positioned in an optical head 306 mounted to a baseplate 310 whose temperature is controlled by a thermoelectric cooler (TEC) 312. The incident laser light 314 is directed out of the optical head 306 through a window 316 into the sample cell 320. The light travels the length of the sample cell 320 twice as it is reflected at the far end of the cell by a flat mirror 322. The returning light is transmitted back through the window 316 and impinges on the photodetector 304. The analyzer shown in FIG. 2 can be modified to incorporate a multi-pass detector head as shown in FIG. 3.

The light source used for the absorption measurements disclosed can emit in the infrared (for example in a wavelength range of approximately 800 to 10,000 nm). The analyzer can utilize a laser whose spectral bandwidth is much narrower than the bandwidth of the absorption lines of interest. Such an arrangement allows for single line absorption spectroscopy in which it is not necessary to scan the entire width of the absorption line or even the peak absorption feature of the line. The wavelength of the laser can be chosen to be one at which there is a resolvable difference in the relative absorbance of water molecules and the other components of the gas to be measured. In one implementation, the laser frequency can be scanned (tuned) back and forth across the chosen absorption wavelength while a photodetector positioned at the opposite end of the beam path length quantifies the light intensity transmitted through the sample as a function of wavelength.

With the laser absorption spectrometers described herein, the tunable laser wavelength can be varied by changing the injection current while keeping the laser temperature constant. The temperature can be controlled by placing the laser in intimate contact with a thermoelectric cooler (Peltier cooler) whose temperature is measured with a thermistor and controlled by a feedback circuit. The control unit of a device, system, or apparatus as described herein can provide process control functions to regulate the system temperature.

In some implementations, an absorption spectrometer system can employ a harmonic spectroscopy technique in connection with its TDL light source. Harmonic spectroscopy as used in the disclosed subject matter involves the modulation of the TDL laser (DFB or VCSEL) wavelength at a high frequency (kHz-MHz) and the detection of the signal at a multiple of the modulation frequency. If the detection is performed at twice the modulation frequency, the term second harmonic or "2f" spectroscopy is used. Advantages to this technique include the minimization of 1/f noise, and the removal of the sloping baseline that is present on TDL spectra (due to the fact that the laser output power increases as the laser injection current increases, and changing the laser injection current is one method by which the laser can be tuned).

Figure 4:
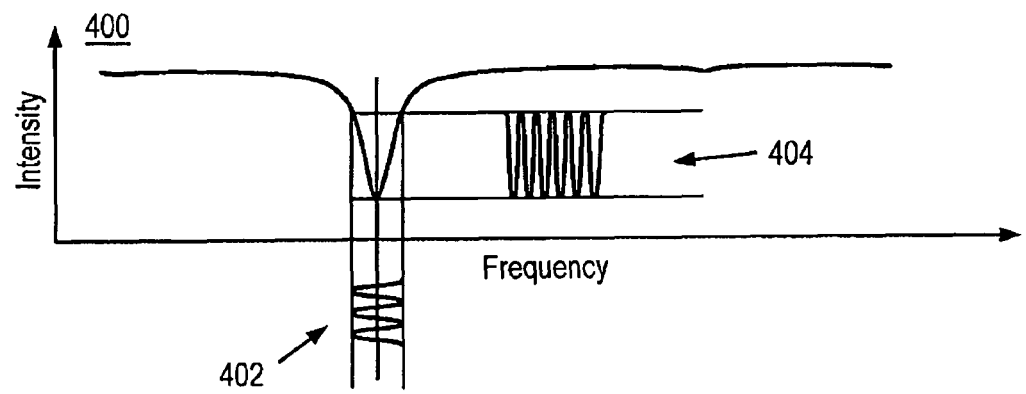
FIG. 4 is a chart that illustrates principles of wavelength modulation spectroscopy.
Figure 5:
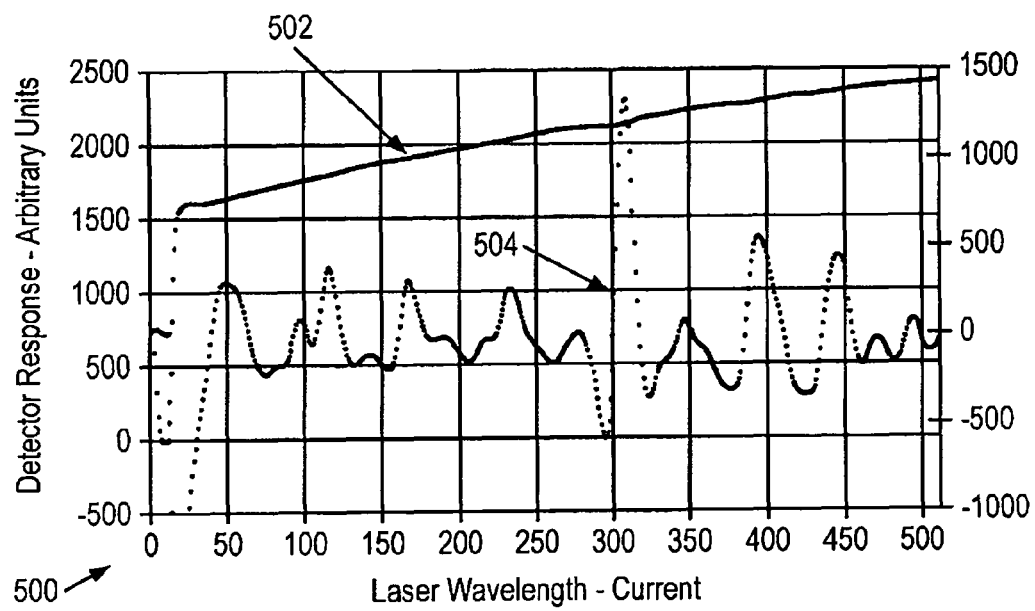
FIG. 5 is a chart showing an example of a DC signal and a 2f signal of wavelength modulation spectroscopy.

FIG. 4 shows an example of a laser scan 400 for use in harmonic spectroscopy. A combination of a slow ramp and a fast sinusoidal modulation of the wavelength 402 is used to drive the diode laser. The photodetector receives this modulated intensity signal 404. The $N^{th}$ harmonic component is resolved by demodulating the received signal. Detection using the signal at the second harmonic (2f) can be used. The 2f lineshape is symmetric and peaks at line center due to the nature of even function. Additionally, the second harmonic (2f) provides the strongest signal of the even-numbered harmonics. FIG. 5 presents a chart 500 of a typical direct current laser intensity signal 502 and a demodulated 2f lineshape 504 vs. frequency. By shifting detection to higher frequency, 2f spectroscopy can significantly reduce 1/f noise thus provides a substantial sensitivity enhancement compared to direct absorption methods.

In another implementation, direct absorption spectroscopy can be used. In this implementation, the laser frequency is tuned over the selected absorption transition and the zero-absorption baseline can be obtained by fitting the regions outside the absorption line to a low-order polynomial. The integrated absorbance is directly proportional to the concentrations of absorbing species in the laser path length as well as the line strength of the transition. The absolute species concentration can be obtained without any calibration Photodetectors used in the disclosed absorption spectrometers depend on the specific wavelengths of the lasers and absorption lines to be measured. One photodetector is an indium gallium arsenide (InGaAs) photodiode sensitive to light in the 1200 to 2600 nm wavelength region. For longer wavelengths, an indium arsenide photodiode, sensitive at room temperature for wavelengths up to approximately 3.6 µm, can be used. Alternatively, indium antimonide detectors are currently available for wavelengths as long as approximately 5.5 µm. Both of the indium devices operate in a photovoltaic mode and do not require a bias current for operation. These photodetectors, which lack low frequency noise, are advantageous for DC or low frequency applications. Such detectors are also advantageous for high speed pulse laser detection, making them particularly useful in trace gas absorption spectroscopy. Other photodetectors, such as for example indium arsenide (InAs), silicon (Si), or germanium (Ge) photodiodes and mercury-cadmium-telluride (MCT) and lead-sulfide (PbS) detectors, may also be used though such devices usually require cooling via thermoelectric coolers (Peltier coolers).

Figure 6:
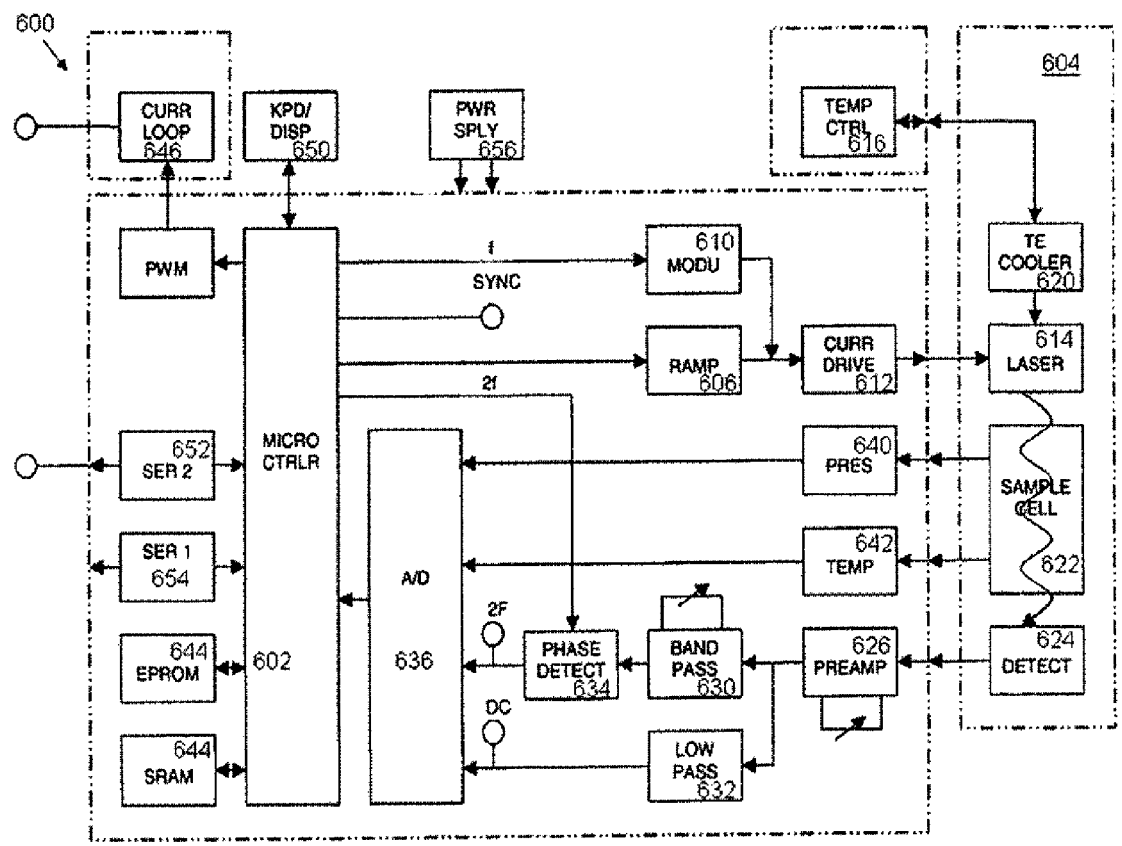
FIG. 6 is a block diagram of a measurement system.

FIG. 6 is a diagram of a sensor system 600 that includes a control and data processing loop system with a microprocessor 602 in communication with a spectrometer 604. On command, a signal is generated by the microprocessor 602 in the form of a rectangular pulse. This pulse is generated periodically. In one implementation, a pulse is generated every 0.25 seconds. Other pulse widths and generation frequencies can be utilized. Each pulse is directed toward a ramp generator 606 that creates a DC signal, an example of which is shown diagrammatically in FIG. 7. In addition to the ramp signal, a modulating sine wave, at for example 7.5 KHz, can be imposed on the current ramp by a modulator 610 for later use in small signal detection. This combined signal is directed to the laser current driver 612 and on to the laser 614 itself.

In this implementation, the laser temperature is held constant by a temperature controller board 616 and the current varied for tuning the laser wavelength. The temperature control loop uses a thermistor (not shown) located close to the laser 614 as the temperature input and a thermoelectric cooler 620 mounted as close (thermally) to the laser 614 as possible. TECs and thermistors can be positioned either directly adjacent to the laser diode or externally but in close contact with the laser diode enclosure. The temperature controller 616 can be used to set the exact laser wavelength such that variation of the driving current can provide the tuning range which can, for example, be in the range of approximately ±0.3 cm$^{-1}$.

Cavity-ring down (CRDS) or Integrated Cavity Output (ICOS) spectroscopy can also be utilized such that a pulsed or CW laser beam is injected into a cavity formed by at least two highly reflective mirror or at least one optical element forming a resonant optical cavity by means of total internal reflection of the light beam. Trace level absorption of a target gas can be detected by utilizing the photon decay time inside this high-finesse optical cavity. In some variations, other cavity-enhanced spectroscopic methods, such as for example integrated cavity output spectroscopy (ICOS), cavity attenuated phase shift spectroscopy (CAPS), cavity output autocorrelation spectroscopy (COAS), or photo-acoustic spectroscopy and the like, can be employed.

Photoacoustic spectroscopy can also be utilized. Some of the energy absorbed by target gas molecules will result in the rise of gas temperature. Temperature fluctuations thus can produce a pressure wave which can be detected by a suitable sensor. By measuring pressure at different wavelengths, a photoacoustic spectrum of the target molecule can be obtained to determine the concentration.

At the beginning of each measurement cycle, the current is held to zero to read the signal produced by the photodetector without laser input and thereby provide the zero for that measurement cycle. This zero can vary a small amount due to slight changes in the detector dark current and the electronic noise so it is advantageous to measure it during each detector cycle. Following determination of the zero, the current is rapidly increased to the laser threshold current. This current is then increased over the remainder of the cycle until the peak current is reached. The beam created from this signal is directed through the sample cell 622 and onto the detector 624 which can be a photodiode, a photodiode array or other comparable detector. The output current from the detector is first amplified by a preamplifier 626. The output of the preamplifier is split and sent to a bandpass filter 630 and a lowpass filter 632. The bandpass filter 630 is a narrowband filter that singles out the 2f signal at 15 KHz and directs it to a lock-in or equivalent amplifier 634 whose reference is set at 15 KHz from a signal provided by the microprocessor. The lock-in amplifier 634 further amplifies the signal and directs it to an A-D board 636 and back into the microprocessor 602. The lowpass filter 632 provides the detector output except the 2f signal. This signal provides the microprocessor 602 with the zero for the system and is also a diagnostic tool.

The signal is developed and recorded by the microprocessor 602 for each cycle of the analyzer. The processor determines the concentration of the gas sample of interest by computing the absorbance of the gas as a ratio between the zero and the measured value of absorbance at the peak of the absorbance line. The absorbance is a function of the gas pressure and temperature in the sample cell 622 which are measured by appropriate means 642 and 644, respectively, whose outputs are supplied to the A/D board 636. The absorbance can be adjusted by a pressure/temperature calibration matrix stored in the microprocessor memory 644. This matrix is developed on an analyzer-by-analyzer basis. Alternatively, one or more corrective calculations can be performed based on measured temperature and pressure in the sample cell.

Once the corrected absorbance value is determined, the concentration can be computed using equation 3. In one implementation, this concentration can be converted into units of, for example lbs/mmscf, averaged four times, and sent to the outputs once per second. Outputs that can be included in this system are a 4-20 mA current loop 646, a visual display 650 and RS-232 or comparable serial ports 652 and 654. Other outputs used include Ethernet, USB, USB-II, RS-485, Fiber Ethernet and simple digital outputs for control of other devices dependent on the measurements made by the analyzer. Power for the system is provided by an appropriately chosen power supply 656.

Figure 7:
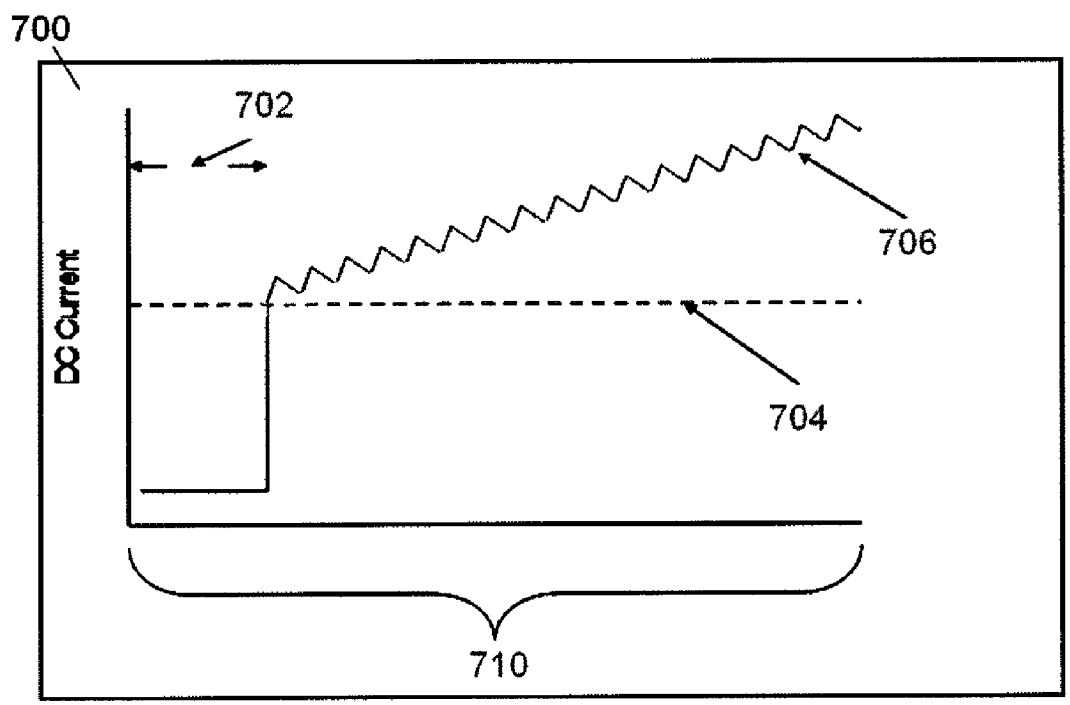
FIG. 7 is a chart showing an example of a laser current drive signal.

The chart of laser current vs. time 700 shown in FIG. 7 illustrates an example of the laser pulse profile that may be used in the disclosed analyzers. For each pulse cycle, a dynamic zero measurement is made during an initial period 702 when the laser current is well below the lasing threshold 704. Then, the laser current is ramped rapidly to at or above the lasing threshold 704, and a modulated laser tuning ramp with an alternating current voltage 706 is added to facilitate the 2f demodulation calculations as described above. At the end of the pulse cycle 710, the process is repeated. In one example, the pulse cycle last approximately 250 milliseconds. Other cycle periods are within the scope of this disclosure.

The light sources utilized herein operate in wavelength ranges where minimal HFC absorption occurs. In some variations, lasers are used as the light sources at wavelengths where moisture does not absorb light (example absorption transitions for measuring of $H_2O$ in HFC are listed in Table 1), thereby minimizing the effects of interference due to the extremely high spectral purity of the laser (narrow line width). The current system can, for example, incorporate a laser (e.g., TDL, DFB, VCSEL, HCSEL, quantum cascade laser, color center laser, etc.) that emits light at or near a wavelength of interest. Table 1 shows sample absorption transitions for measurement of $H_2O$ in HFC.

TABLE 1

| | | |
|---|---|---|
| 1359.5 nm | 1856.7 nm | 2605.6 nm |
| 1361.7 nm | 1859.8 nm | 2620.5 nm |
| 1368.6 nm | 1877.1 nm | 2626.7 nm |
| 1371.0 nm | 1890.3 nm | 2630.6 nm |
| 1392.0 nm | 1899.7 nm | 2665.1 nm |
| 1836.3 nm | 1903.0 nm | 2676.0 nm |
| 1840.0 nm | 1905.4 nm | 2711.2 nm |
| 1842.1 nm | 2573.6 nm | 2724.2 nm |
| 1847.1 nm | 2583.9 nm | 2735.0 nm |
| 1854.0 nm | 2596.0 nm | 2740.0 nm |

Figure 8:
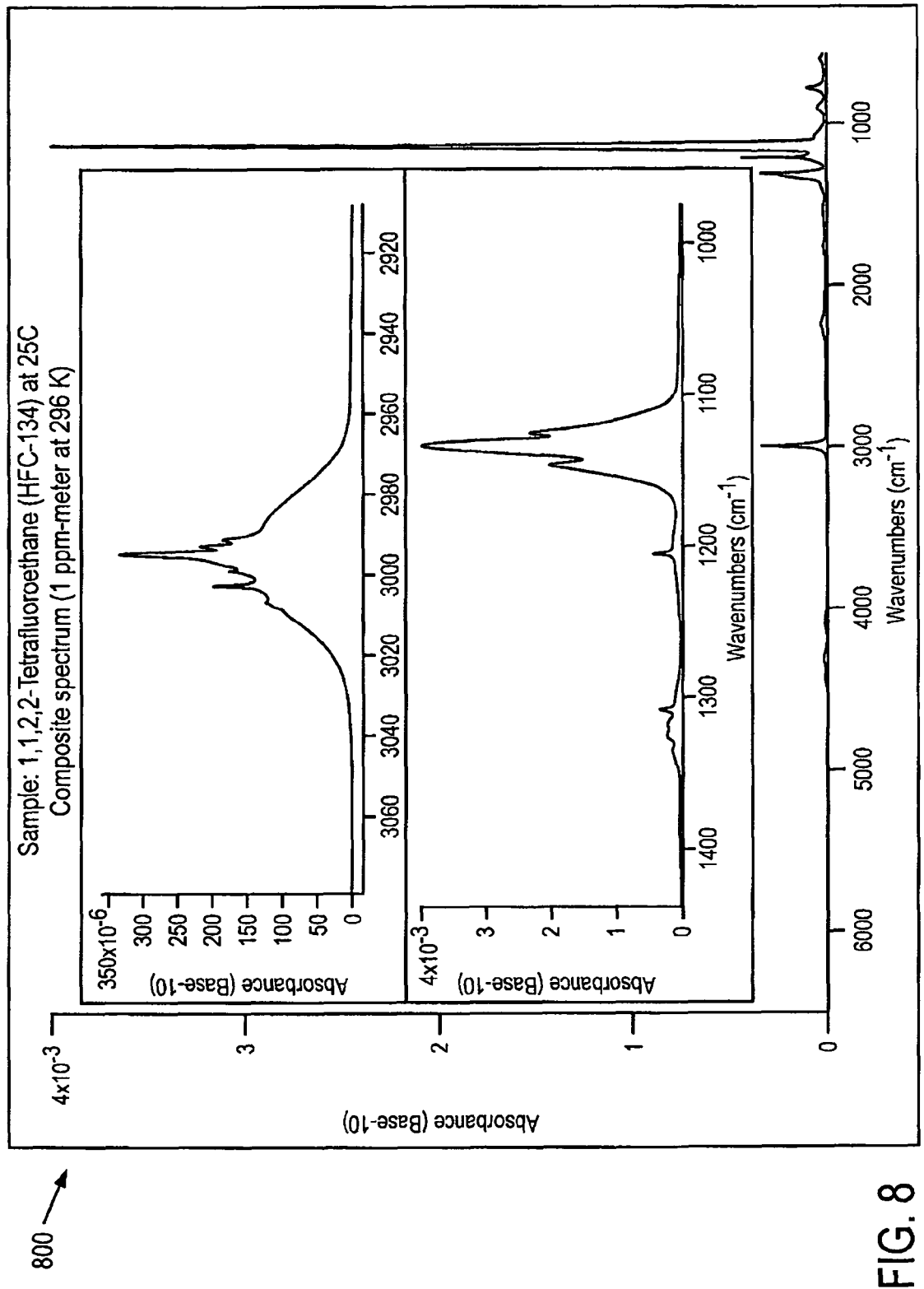
FIG. 8 is a diagram illustrating an absorption spectrum of HFC-134A between 1.5 and 10 μm.
Figure 9:
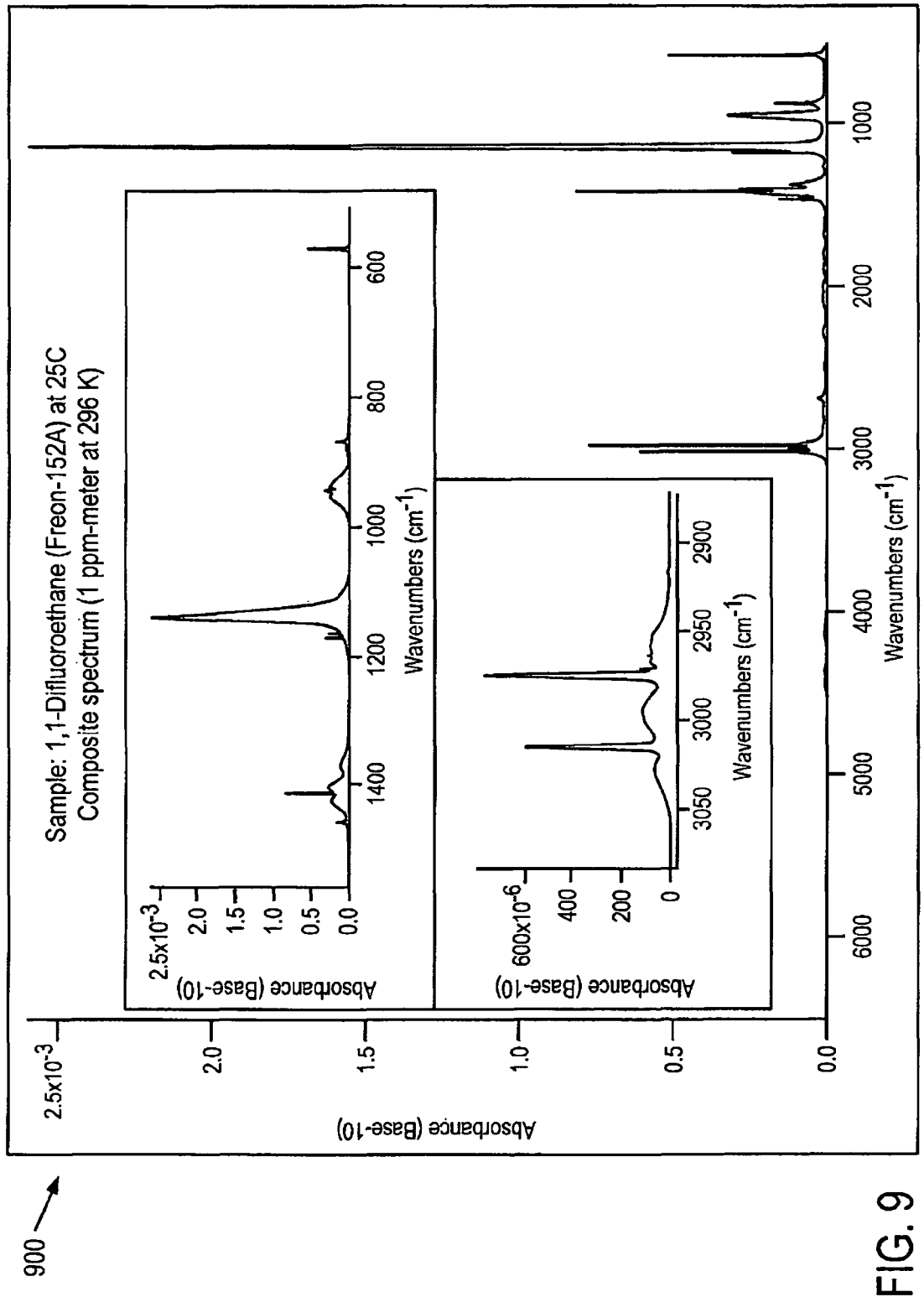
FIG. 9 is a diagram illustrating an absorption spectrum of HFC-152A between 1.5 and 10 μm.
Figure 10:
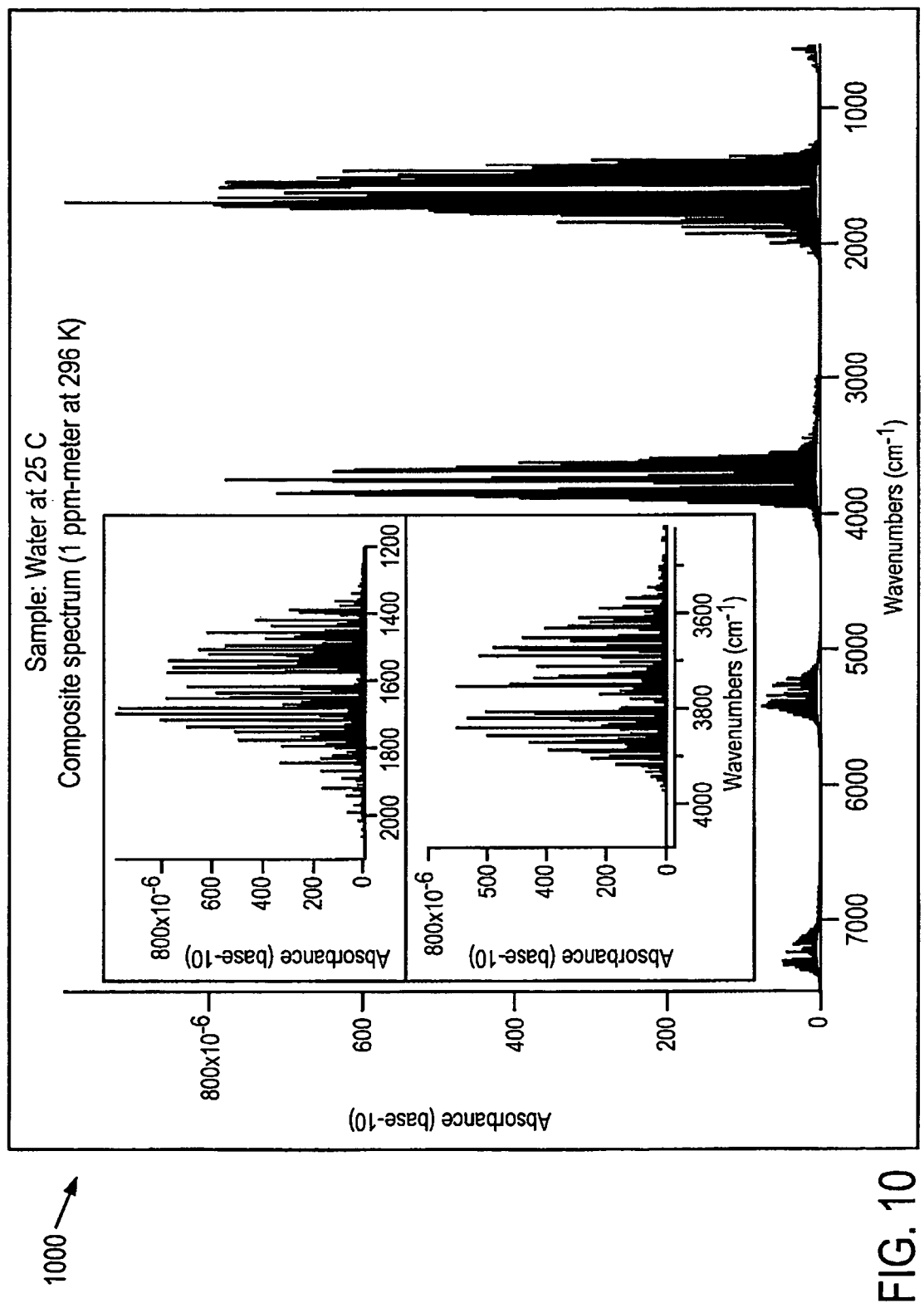
FIG. 10 is a diagram illustrating absorption spectrum of $H_2O$ between 1.5 and 10 μm.

The present system can measure moisture at the absorption bands where absorption by HFCs and the infrared-absorbing constituents within air are very weak or non-existent (e.g., near 1.4, 1.9, and 2.7 µm (Table 1), etc.). FIGS. 8 and 9 are example diagrams 800, 900 that illustrate absorption spectra of two common HFCs (HFC-134A and HFC 152A). FIG. 10 is a diagram 1000 showing absorption spectra of moisture. As can be seen, the moisture transitions at the above mentioned $H_2O$ absorption wavelengths are well isolated from interferences of HFCs in general and 134A and 152A specifically.

Figure 11:
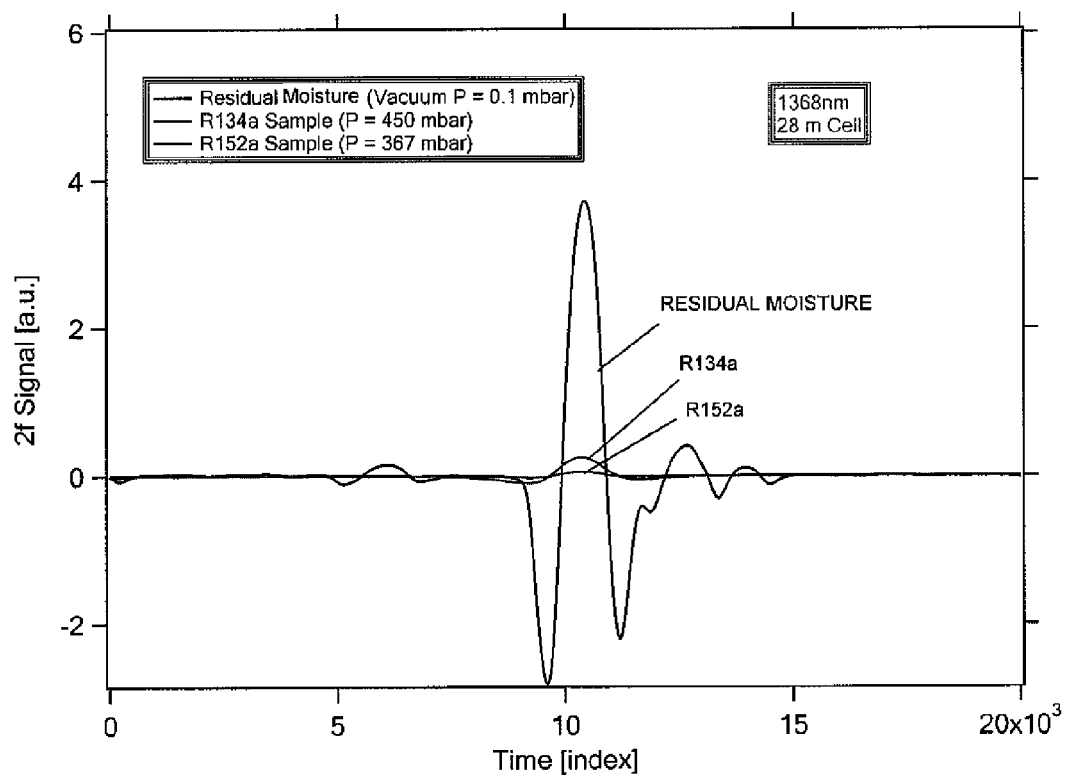
FIG. 11 is a diagram illustrating spectra of HFC-134A and HFC-152A with moisture at λ~1368 nm.
Figure 12:
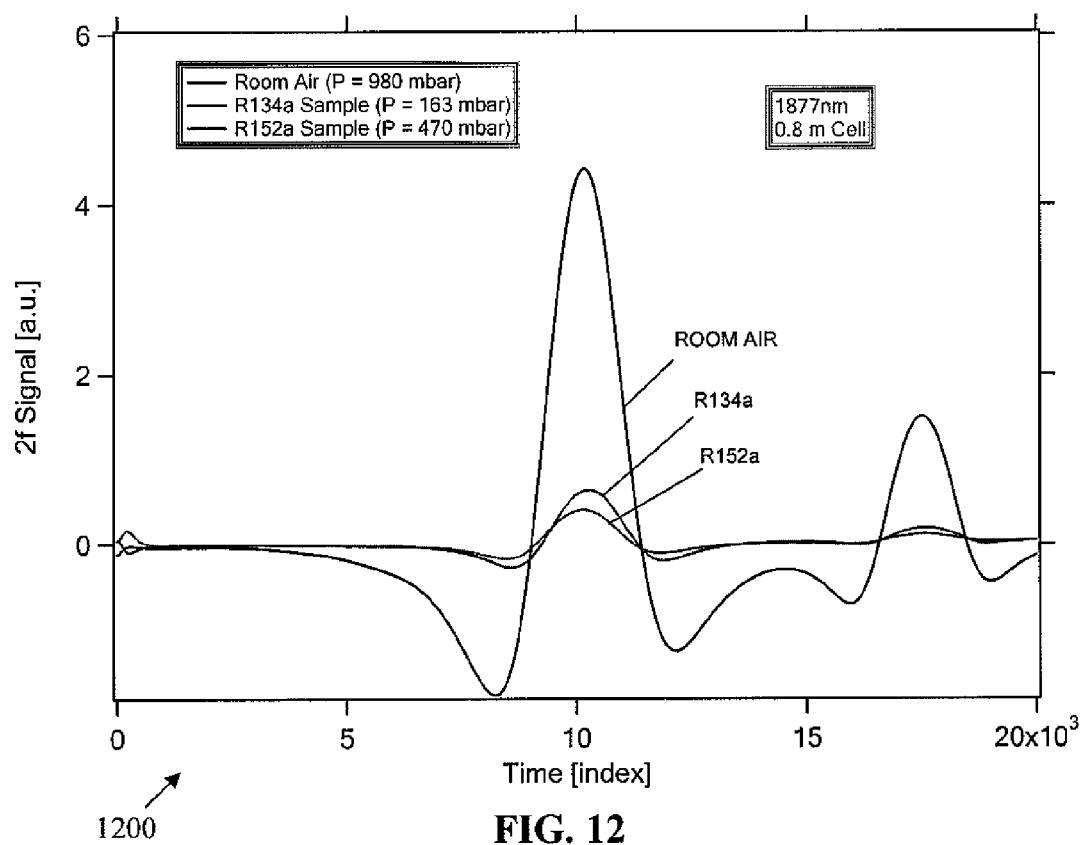
FIG. 12 is a diagram illustrating spectra of HFC-134A and HFC-152A with moisture at λ~1877 nm.

Moisture in HFC-134A and HFC-152A can be measured at a precision of $\leq 500$ ppb or better at the wavelengths of 1368 nm and 1877 nm. FIG. 11 is a diagram 1100 that shows the overlapping spectra of HFC-134A, HFC-152A and $H_2O$ in the region of 1368 nm. FIG. 12 is a diagram 1200 that shows the overlapping spectra of HFC-134A, HFC-152A and $H_2O$ in the region of 1877 nm. These spectra are given as representative of the various wavelengths where moisture can be measured in the HFCs listed here. The difference between the absorption peak of water and those of HFC-134A and 152A are clear. By using the using a light source such as a DFB laser, the 2f spectroscopic technique, and then peak seeking the "2f" signal, a clear measure can be made. The technique can also be implemented at 1.368 µm using an absorption cell with a total pathlength of more than 0.25 m depending on the individual absorption of the HFC (if any) at the laser wavelength. For measures of higher concentrations of $H_2O$, in the % level, this cell can be as short as 1 cm. For very low levels of moisture, a precise measurement can be enhanced by placing the spectrometer in a thermally controlled enclosure whose interior is insulated and temperature is held above 30° C. in conditions where the environment can vary from −15° C. to +60° C. The results of this technique yield the curves shown in FIG. 11.

This measurement can also be made if the light source operates at a wavelength of 1877 nm, the absorption cell is more than 0.25 m long and has an operating pressure of ~1 Bar and that the cell is maintained to a constant temperature within ±5° C. The results of this variation yield the curves shown in FIG. 12.

It will be appreciated that the current systems and techniques are applicable to all refrigerants, and as such, unless otherwise noted, the current disclosure should not be construed to be limited any particular refrigerants. Other refrigerants which may be detected are listed in Table 2 below.

TABLE 2

| Designation | Name | Formula | CAS number |
|---|---|---|---|
| R-10 | Tetrachloromethane | CCl4 | 56-23-5 |
| R-11 | Trichlorofluoromethane | CCl3F | 75-69-4 |
| R-12 | Dichlorodifluoromethane | CCl2F2 | 75-71-8 |
| R-12B1 | Bromochlorodifluoromethane | CBrClF2 | 353-59-3 |
| R-12B2 | Dibromodifluoromethane | CBr2F2 | 75-61-6 |
| R-13 | Chlorotrifluoromethane | CClF3 | 75-72-9 |
| R-13B1 | Bromotrifluoromethane | CF3Br | 75-63-8 |
| R-14 | Carbon tetrafluoride | CF4 | 75-73-0 |
| R-20 | Trichloromethane | CHCl3 | 67-66-3 |
| R-21 | Dichlorofluoromethane | CHFCl2 | 75-43-4 |
| R-22 | Chlorodifluoromethane | CHClF2 | 75-45-6 |
| R-22B1 | Bromodifluoromethane | CHBrF2 | 1511-62-2 |
| R-23 | Trifluoromethane | CHF3 | 75-46-7 |
| R-30 | Dichloromethane | CH2Cl2 | 75-09-2 |
| R-31 | Chlorofluoromethane | CH2FCl | 593-70-4 |
| R-32 | Difluoromethane | CH2F2 | 75-10-5 |
| R-40 | Chloromethane | CH3Cl | 74-87-3 |
| R-41 | Fluoromethane | CH3F | 593-53-3 |
| R-50 | Methane | CH4 | 74-82-8 |
| R-110 | Hexachloroethane | C2Cl6 | 67-72-1 |
| R-111 | Pentachlorofluoroethane | C2FCl5 | 354-56-3 |
| R-112 | 1,1,2,2-Tetrachloro-1,2-difluoroethane | C2F2Cl4 | 76-12-0 |
| R-112a | 1,1,1,2-Tetrachloro-2,2-difluoroethane | C2F2Cl4 | 76-11-9 |
| R-113 | 1,1,2-Trichlorotrifluoroethane | C2F3Cl3 | 76-13-1 |
| R-113a | 1,1,1-Trichlorotrifluoroethane | C2F3Cl3 | 354-58-5 |
| R-114 | 1,2-Dichlorotetrafluoroethane | C2F4Cl2 | 76-14-2 |
| R-114a | 1,1-Dichlorotetrafluoroethane | C2F4Cl2 | 374-07-2 |
| R-114B2 | Dibromotetrafluoroethane | C2F4Br2 | 124-73-2 |
| R-115 | Chloropentafluoroethane | C2F5Cl | 76-15-3 |
| R-116 | Hexafluoroethane | C2F6 | 76-16-4 |
| R-120 | Pentachloroethane | C2HCl5 | 76-01-7 |
| R-121 | 1,1,2,2-Tetrachloro-1-fluoroethane | C2HFCl4 | 354-14-3 |
| R-121a | 1,1,1,2-Tetrachloro-2-fluoroethane | C2HFCl4 | 354-11-0 |
| R-122 | 1,1,2-Trichloro-2,2-difluoroethane | C2HF2Cl3 | 354-21-2 |
| R-122a | 1,1,2-Trichloro-1,2-difluoroethane | C2HF2Cl3 | 354-15-4 |
| R-122b | 1,1,1-Trichloro-2,2-difluoroethane | C2HF2Cl3 | 354-12-1 |
| R-123 | 2,2-Dichloro-1,1,1-trifluoroethane | C2F3Cl2 | 306-83-2 |
| R-123a | 1,2-Dichloro-1,1,2-trifluoroethane | C2F3Cl2 | 354-23-4 |
| R-123b | 1,1-Dichloro-1,2,2-trifluoroethane | C2F3Cl2 | 812-04-4 |
| R-124 | 2-Chloro-1,1,1,2-tetrafluoroethane | C2HF4Cl | 2837-89-0 |
| R-124a | 1-Chloro-1,1,2,2-tetrafluoroethane | C2HF4Cl | 354-25-6 |
| R-125 | Pentafluoroethane | C2HF5 | 354-33-6 |
| R-E125 | (Difluoromethoxy)(trifluoro)methane | C2HF5O | 3822-68-2 |
| R-130 | 1,1,2,2-Tetrachloroethane | C2H2Cl4 | 79-34-5 |
| R-130a | 1,1,1,2-Tetrachloroethane | C2H2Cl4 | 630-20-6 |
| R-131 | 1,1,2-trichloro-2-fluoroethane | C2H2FCl3 | 359-28-4 |
| R-131a | 1,1,2-trichloro-1-fluoroethane | C2H2FCl3 | 811-95-0 |
| R-131b | 1,1,1-trichloro-2-fluoroethane | C2H2FCl3 | 2366-36-1 |
| R-132 | Dichlorodifluoroethane | C2H2F2Cl2 | 25915-78-0 |
| R-132a | 1,1-Dichloro-2,2-difluoroethane | C2H2F2Cl2 | 471-43-2 |
| R-132b | 1,2-Dichloro-1,1-difluoroethane | C2H2F2Cl2 | 1649-08-7 |
| R-132c | 1,1-Dichloro-1,2-difluoroethane | C2H2F2Cl2 | 1842-05-3 |
| R-132bB2 | 1,2-Dibromo-1,1-difluoroethane | C2H2Br2F2 | 75-82-1 |
| R-133 | 1-Chloro-1,2,2-Trifluoroethane | C2H2F3Cl | 431-07-2 |
| R-133a | 1-Chloro-2,2,2-Trifluoroethane | C2H2F3Cl | 75-88-7 |
| R-133b | 1-Chloro-1,1,2-Trifluoroethane | C2H2F3Cl | 421-04-5 |
| R-134 | 1,1,2,2-Tetrafluoroethane | C2H2F4 | 359-35-3 |
| R-134a | 1,1,1,2-Tetrafluoroethane | C2H2F4 | 811-97-2 |
| R-E134 | Bis(difluoromethyl)ether | C2H2F4O | 1691-17-4 |
| R-140 | 1,1,2-Trichloroethane | C2H3Cl3 | 79-00-5 |
| R-140a | 1,1,1-Trichloroethane | C2H3Cl3 | 71-55-6 |
| R-141 | 1,2-Dichloro-1-fluoroethane | C2H3FCl2 | 430-57-9 |
| R-141B2 | 1,2-Dibromo-1-fluoroethane | C2H3Br2F | 358-97-4 |

TABLE 2-continued

| Designation | Name | Formula | CAS number |
|---|---|---|---|
| R-141a | 1,1-Dichloro-2-fluoroethane | C2H3FCl2 | 430-53-5 |
| R-141b | 1,1-Dichloro-1-fluoroethane | C2H3FCl2 | 1717-00-6 |
| R-142 | Chlorodifluoroethane | C2H3F2Cl | 25497-29-4 |
| R-142a | 1-Chloro-1,2-difluoroethane | C2H3F2Cl | 25497-29-4 |
| R-142b | 1-Chloro-1,1-difluoroethane | C2H3F2Cl | 75-68-3 |
| R-143 | 1,1,2-Trifluoroethane | C2H3F3 | 430-66-0 |
| R-143a | 1,1,1-Trifluoroethane | C2H3F3 | 420-46-2 |
| R-143m | Methyl trifluoromethyl ether | C2H3F3O | 421-14-7 |
| R-E143a | 2,2,2-Trifluoroethyl methyl ether | C3H5F3O | 460-43-5 |
| R-150 | 1,2-Dichloroethane | C2H4Cl2 | 107-06-2 |
| R-150a | 1,1-Dichloroethane | C2H4Cl2 | 75-34-3 |
| R-151 | Chlorofluoroethane | C2H4ClF | 110587-14-9 |
| R-151a | 1-Chloro-1-fluoroethane | C2H4ClF | 1615-75-4 |
| R-152 | 1,2-Difluoroethane | C2H4F2 | 624-72-6 |
| R-152a | 1,1-Difluoroethane | C2H4F2 | 75-37-6 |
| R-160 | Chloroethane | C2H5Cl | 75-00-3 |
| R-161 | Fluoroethane | C2H5F | 353-36-6 |
| R-170 | Ethane | C2H6 | 74-84-0 |
| R-211 | 1,1,1,2,2,3,3-Heptachloro-3-fluoropropane | C3FCl7 | 422-78-6 |
| R-212 | Hexachlorodifluoropropane | C3F2Cl6 | 76546-99-3 |
| R-213 | 1,1,1,3,3-Pentachloro-2,2,3-trifluoropropane | C3F3Cl5 | 2354-06-5 |
| R-214 | 1,2,2,3-Tetrachloro-1,1,3,3-tetrafluoropropane | C3F4Cl4 | 2268-46-4 |
| R-215 | 1,1,1-Trichloro-2,2,3,3,3-pentafluoropropane | C3F5Cl3 | 4259-43-2 |
| R-216 | 1,2-Dichloro-1,1,2,3,3,3-hexafluoropropane | C3F6Cl2 | 661-97-2 |
| R-216ca | 1,3-Dichloro-1,1,2,2,3,3-hexafluoropropane | C3F6Cl2 | 662-01-1 |
| R-217 | 1-Chloro-1,1,2,2,3,3,3-heptafluoropropane | C3F7Cl | 422-86-6 |
| R-217ba | 2-Chloro-1,1,1,2,3,3,3-heptafluoropropane | C3F7Cl | 76-18-6 |
| R-218 | Octafluoropropane | C3F8 | 76-19-7 |
| R-221 | 1,1,1,2,2,3-Hexachloro-3-fluoropropane | C3HFCl6 | 422-26-4 |
| R-222 | Pentachlorodifluoropropane | C3HF2Cl5 | 134237-36-8 |
| R-222c | 1,1,1,3,3-Pentachloro-2,2-difluoropropane | C3HF2Cl5 | 422-49-1 |
| R-223 | Tetrachlorotrifluoropropane | C3HF3Cl4 | 134237-37-9 |
| R-223ca | 1,1,3,3-Tetrachloro-1,2,2-trifluoropropane | C3HF3Cl4 | 422-52-6 |
| R-223cb | 1,1,1,3-Tetrachloro-2,2,3-trifluoropropane | C3HF3Cl4 | 422-50-4 |
| R-224 | Trichlorotetrafluoropropane | C3HF4Cl3 | 134237-38-0 |
| R-224ca | 1,3,3-Trichloro-1,1,2,2-tetrafluoropropane | C3HF4Cl3 | 422-54-8 |
| R-224cb | 1,1,3-Trichloro-1,2,2,3-tetrafluoropropane | C3HF4Cl3 | 422-53-7 |
| R-224cc | 1,1,1-Trichloro-2,2,3,3-tetrafluoropropane | C3HF4Cl3 | 422-51-5 |
| R-225 | Dichloropentafluoropropane | C3HF5Cl2 | 127564-92-5 |
| R-225aa | 2,2-Dichloro-1,1,1,3,3-pentafluoropropane | C3HF5Cl2 | 128903-21-9 |
| R-225ba | 2,3-Dichloro-1,1,1,2,3-pentafluoropropane | C3HF5Cl2 | 422-48-0 |
| R-225bb | 1,2-Dichloro-1,1,2,3,3-pentafluoropropane | C3HF5Cl2 | 422-44-6 |
| R-225ca | 3,3-Dichloro-1,1,1,2,2-pentafluoropropane | C3HF5Cl2 | 422-56-0 |
| R-225cb | 1,3-Dichloro-1,1,2,2,3-pentafluoropropane | C3HF5Cl2 | 507-55-1 |
| R-225cc | 1,1-Dichloro-1,2,2,3,3-pentafluoropropane | C3HF5Cl2 | 13474-88-9 |
| R-225da | 1,2-Dichloro-1,1,3,3,3-pentafluoropropane | C3HF5Cl2 | 431-86-7 |
| R-225ea | 1,3-Dichloro-1,1,2,3,3-pentafluoropropane | C3HF5Cl2 | 136013-79-1 |
| R-225eb | 1,1-Dichloro-1,2,3,3,3-pentafluoropropane | C3HF5Cl2 | 111512-56-2 |
| R-226 | Chlorohexafluoropropane | C3HF6Cl | 134308-72-8 |
| R-226ba | 2-Chloro-1,1,1,2,3,3-hexafluoropropane | C3HF6Cl | 51346-64-6 |
| R-226ca | 3-Chloro-1,1,1,2,2,3-hexafluoropropane | C3HF6Cl | 422-57-1 |
| R-226cb | 1-Chloro-1,1,2,2,3,3-hexafluoropropane | C3HF6Cl | 422-55-9 |
| R-226da | 2-Chloro-1,1,1,3,3,3-hexafluoropropane | C3HF6Cl | 431-87-8 |
| R-226ea | 1-Chloro-1,1,2,3,3,3-hexafluoropropane | C3HF6Cl | 359-58-0 |
| R-227ca | 1,1,2,2,3,3,3-Heptafluoropropane | C3HF7 | 2252-84-8 |
| R-227ca2 | Trifluoromethyl 1,1,2,2-tetrafluoroethyl ether | C3HF7O | 2356-61-8 |
| R-227ea | 1,1,1,2,3,3,3-Heptafluoropropane | C3HF7 | 431-89-0 |
| R-227me | Trifluoromethyl 1,2,2,2-tetrafluoroethyl ether | C3HF7O | 2356-62-9 |
| R-231 | Pentachlorofluoropropane | C3H2FCl5 | 134190-48-0 |
| R-232 | Tetrachlorodifluoropropane | C3H2F2Cl4 | 134237-39-1 |
| R-232ca | 1,1,3,3-Tetrachloro-2,2-difluoropropane | C3H2F2Cl4 | 1112-14-7 |
| R-232cb | 1,1,1,3-Tetrachloro-2,2-difluoropropane | C3H2F2Cl4 | 677-54-3 |
| R-233 | Trichlorotrifluoropropane | C3H2F3Cl3 | 134237-40-4 |
| R-233ca | 1,1,3-Trichloro-2,2,3-trifluoropropane | C3H2F3Cl3 | 131221-36-8 |
| R-233cb | 1,1,3-Trichloro-1,2,2-trifluoropropane | C3H2F3Cl3 | 421-99-8 |
| R-233cc | 1,1,1-Trichloro-2,2,3-trifluoropropane | C3H2F3Cl3 | 131211-71-7 |
| R-234 | Dichlorotetrafluoropropane | C3H2F4Cl2 | 127564-83-4 |
| R-234aa | 2,2-Dichloro-1,1,3,3-tetrafluoropropane | C3H2F4Cl2 | |
| R-234ab | 2,2-Dichloro-1,1,1,3-tetrafluoropropane | C3H2F4Cl2 | |
| R-234ba | 1,2-Dichloro-1,2,3,3-tetrafluoropropane | C3H2F4Cl2 | |
| R-234bb | 2,3-Dichloro-1,1,1,2-tetrafluoropropane | C3H2F4Cl2 | |
| R-234bc | 1,2-Dichloro-1,1,2,3-tetrafluoropropane | C3H2F4Cl2 | |
| R-234ca | 1,3-Dichloro-1,2,2,3-tetrafluoropropane | C3H2F4Cl2 | 70341-81-0 |
| R-234cb | 1,1-Dichloro-2,2,3,3-tetrafluoropropane | C3H2F4Cl2 | 4071-01-6 |
| R-234cc | 1,3-Dichloro-1,1,2,2-tetrafluoropropane | C3H2F4Cl2 | 422-00-5 |
| R-234cd | 1,1-Dichloro-1,2,2,3-tetrafluoropropane | C3H2F4Cl2 | 70192-63-1 |
| R-234da | 2,3-Dichloro-1,1,1,3-tetrafluoropropane | C3H2F4Cl2 | 146916-90-7 |

TABLE 2-continued

| Designation | Name | Formula | CAS number |
|---|---|---|---|
| R-234fa | 1,3-Dichloro-1,1,3,3-tetrafluoropropane | C3H2F4Cl2 | 76140-39-1 |
| R-234fb | 1,1-Dichloro-3,3,3,1-tetrafluoropropane | C3H2F4Cl2 | |
| R-235 | Chloropentafluoropropane | C3H2F5Cl | 134237-41-5 |
| R-235ca | 1-Chloro-1,2,2,3,3-pentafluoropropane | C3H2F5Cl | 28103-66-4 |
| R-235cb | 3-Chloro-1,1,1,2,3-pentafluoropropane | C3H2F5Cl | 422-02-6 |
| R-235cc | 1-Chloro-1,1,2,2,3-pentafluoropropane | C3H2F5Cl | 679-99-2 |
| R-235da | 2-Chloro-1,1,1,3,3-pentafluoropropane | C3H2F5Cl | 134251-06-2 |
| R-235fa | 1-Chloro-1,1,3,3,3-pentafluoropropane | C3H2F5Cl | 677-55-4 |
| R-236cb | 1,1,1,2,2,3-Hexafluoropropane | C3H2F6 | 677-56-5 |
| R-236ea | 1,1,1,2,3,3-Hexafluoropropane | C3H2F6 | 431-63-0 |
| R-236fa | 1,1,1,3,3,3-Hexafluoropropane | C3H2F6 | 690-39-1 |
| R-236me | 1,2,2,2-Tetrafluoroethyl difluoromethyl ether | C3H2F6O | 57041-67-5 |
| R-FE-36 | Hexafluoropropane | C3H2F6 | 359-58-0 |
| R-241 | Tetrachlorofluoropropane | C3H3FCl4 | 134190-49-1 |
| R-242 | Trichlorodifluoropropane | C3H3F2Cl3 | 134237-42-6 |
| R-243 | Dichlorotrifluoropropane | C3H3F3Cl2 | 134237-43-7 |
| R-243ca | 1,3-Dichloro-1,2,2-trifluoropropane | C3H3F3Cl2 | 67406-68-2 |
| R-243cb | 1,1-Dichloro-2,2,3-trifluoropropane | C3H3F3Cl2 | 70192-70-0 |
| R-243cc | 1,1-Dichloro-1,2,2-trifluoropropane | C3H3F3Cl2 | 7125-99-7 |
| R-243da | 2,3-Dichloro-1,1,1-trifluoropropane | C3H3F3Cl2 | 338-75-0 |
| R-243ea | 1,3-Dichloro-1,2,3-trifluoropropane | C3H3F3Cl2 | |
| R-243ec | 1,3-Dichloro-1,1,2-trifluoropropane | C3H3F3Cl2 | |
| R-244 | Chlorotetrafluoropropane | C3H3F4Cl | 134190-50-4 |
| R-244ba | 2-Chloro-1,2,3,3-tetrafluoropropane | C3H3F4Cl | |
| R-244bb | 2-Chloro-1,1,1,2-tetrafluoropropane | C3H3F4Cl | 421-73-8 |
| R-244ca | 3-Chloro-1,1,2,2-tetrafluoropropane | C3H3F4Cl | 679-85-6 |
| R-244cb | 1-Chloro-1,2,2,3-tetrafluoropropane | C3H3F4Cl | 67406-66-0 |
| R-244cc | 1-Chloro-1,1,2,2-tetrafluoropropane | C3H3F4Cl | 421-75-0 |
| R-244da | 2-Chloro-1,1,3,3-tetrafluoropropane | C3H3F4Cl | 19041-02-2 |
| R-244db | 2-Chloro-1,1,1,3-tetrafluoropropane | C3H3F4Cl | 117970-90-8 |
| R-244ea | 3-Chloro-1,1,2,3-tetrafluoropropane | C3H3F4Cl | |
| R-244eb | 1-Chloro-1,1,2,3-tetrafluoropropane | C3H3F4Cl | |
| R-244ec | 1-Chloro-1,1,2,3-tetrafluoropropane | C3H3F4Cl | |
| R-244fa | 3-Chloro-1,1,1,3-tetrafluoropropane | C3H3F4Cl | |
| R-244fb | 1-Chloro-1,1,3,3-tetrafluoropropane | C3H3F4Cl | 2730-64-5 |
| R-245ca | 1,1,2,2,3-Pentafluoropropane | C3H3F5 | 679-86-7 |
| R-245cb | Pentafluoropropane | C3H3F5 | 1814-88-6 |
| R-245ea | 1,1,2,3,3-Pentafluoropropane | C3H3F5 | 24270-66-4 |
| R-245eb | 1,1,1,2,3-Pentafluoropropane | C3H3F5 | 431-31-2 |
| R-245fa | 1,1,1,3,3-Pentafluoropropane | C3H3F5 | 460-73-1 |
| R-245mc | Methyl pentafluoroethyl ether | C3H3F5O | 22410-44-2 |
| R-245mf | Difluoromethyl 2,2,2-trifluoroethyl ether | C3H3F5O | 1885-48-9 |
| R-245qc | Difluoromethyl 1,1,2-trifluoroethyl ether | C3H3F5O | 69948-24-9 |
| R-251 | Trichlorofluoropropane | C3H4FCl3 | 134190-51-5 |
| R-252 | Dichlorodifluoropropane | C3H4F2Cl2 | 134190-52-6 |
| R-252ca | 1,3-Dichloro-2,2-difluoropropane | C3H4F2Cl2 | 1112-36-3 |
| R-252cb | 1,1-Dichloro-2,2-difluoropropane | C3H4F2Cl2 | 1112-01-2 |
| R-252dc | 1,2-Dichloro-1,1-difluoropropane | C3H4F2Cl2 | |
| R-252ec | 1,1-Dichloro-1,2-difluoropropane | C3H4F2Cl2 | |
| R-253 | Chlorotrifluoropropane | C3H4F3Cl | 134237-44-8 |
| R-253ba | 2-Chloro-1,2,3-trifluoropropane | C3H4F3Cl | |
| R-253bb | 2-Chloro-1,1,2-trifluoropropane | C3H4F3Cl | |
| R-253ca | 1-Chloro-2,2,3-trifluoropropane | C3H4F3Cl | 56758-54-4 |
| R-253cb | 1-Chloro-1,2,2-trifluoropropane | C3H4F3Cl | 70192-76-6 |
| R-253ea | 3-Chloro-1,1,2-trifluoropropane | C3H4F3Cl | |
| R-253eb | 1-Chloro-1,2,3-trifluoropropane | C3H4F3Cl | |
| R-253ec | 1-Chloro-1,1,2-trifluoropropane | C3H4F3Cl | |
| R-253fa | 3-Chloro-1,3,3-trifluoropropane | C3H4F3Cl | |
| R-253fb | 3-Chloro-1,1,1-trifluoropropane | C3H4F3Cl | 460-35-5 |
| R-253fc | 1-Chloro-1,1,3-trifluoropropane | C3H4F3Cl | |
| R-254cb | 1,1,2,2-Tetrafluoropropane | C3H4F4 | 40723-63-5 |
| R-254pc | Methyl 1,1,2,2-tetrafluoroethyl ether | C3H4F4O | 425-88-7 |
| R-261 | Dichlorofluoropropane | C3H5FCl2 | 134237-45-9 |
| R-261ba | 1,2-Dichloro-2-fluoropropane | C3H5FCl2 | 420-97-3 |
| R-262 | Chlorodifluoropropane | C3H5F2Cl | 134190-53-7 |
| R-262ca | 1-Chloro-2,2-difluoropropane | C3H5F2Cl | 420-99-5 |
| R-262fa | 3-Chloro-1,1-difluoropropane | C3H5F2Cl | |
| R-262fb | 1-Chloro-1,3-difluoropropane | C3H5F2Cl | |
| R-263 | Trifluoropropane | C3H5F3 | |
| R-271 | Chlorofluoropropane | C3H6FCl | 134190-54-8 |
| R-271b | 2-Chloro-2-fluoropropane | C3H6FCl | 420-44-0 |
| R-271d | 2-Chloro-1-fluoropropane | C3H6FCl | |
| R-271fb | 1-Chloro-1-fluoropropane | C3H6FCl | |
| R-272 | Difluoropropane | C3H6F2 | |
| R-281 | Fluoropropane | C3H7F | |
| R-290 | Propane | C3H8 | 74-98-6 |
| R-C316 | Dichlorohexafluorocyclobutane | C4Cl2F6 | 356-18-3 |

TABLE 2-continued

| Designation | Name | Formula | CAS number |
|---|---|---|---|
| R-C317 | Chloroheptafluorocyclobutane | C4ClF7 | 377-41-3 |
| R-C318 | Octafluorocyclobutane | C4F8 | 115-25-3 |
| R-3-1-10 | Decafluorobutane | C4F10 | |
| R-329ccb | | | 375-17-7 |
| R-338eea | | | 75995-72-1 |
| R-347ccd | | | 662-00-0 |
| R-347mcc | Perfluoropropyl methyl ether | C4H3F7O | 375-03-1 |
| R-347mmy | Perfluoroisopropyl methyl ether | C4H3F7O | 22052-84-2 |
| R-356mcf | | | |
| R-356mffm | | | |
| R-365mfc | 1,1,1,3,3-Pentafluorobutane | C4H5F5 | |
| R- | Tetradecafluorohexane | C6F14 | 355-42-0 |
| R-400 | R-12/R-114 (60/40 wt %) | binary blend | |
| R-401A | R-22/R-152a/R-124 (53/13/34) | | |
| R-401B | R-22/R-152a/R-124 (61/11/28) | | |
| R-401C | R-22/R-152a/R-124 (33/15/52) | | |
| R-402A | R-125/R-290/R-22 (60/2/38) | | |
| R-402B | R-125/R-290/R-22 (38/2/60) | | |
| R-403A | R-290/R-22/R-218 (5/75/20) | | |
| R-403B | R-290/R-22/R-218 (5/56/39) | | |
| R-404A | R-125/R-143a/R-134a (44/52/4) | | |
| R-405A | R-22/R-152a/R-142b/R-C318 (45/7/5.5/42.5) | | |
| R-406A | R-22/R-600a/R-142b (55/04/41) | | |
| R-407A | R-32/R-125/R-134a (20/40/40) | | |
| R-407B | R-32/R-125/R-134a (10/70/20) | | |
| R-407C | R-32/R-125/R-134a (23/25/52) | | |
| R-407D | R-32/R-125/R-134a (15/15/70) | | |
| R-407E | R-32/R-125/R-134a (25/15/60) | | |
| R-408A | R-125/R-143a/R-22 (7/46/47) | | |
| R-409A | R-22/R-124/R-142b (60/25/15) | | |
| R-409B | R-22/R-124/R-142b (65/25/10) | | |
| R-410A | R-32/R-125 (50/50) | | |
| R-410B | R-32/R-125 (45/55) | | |
| R-411A | R-1270/R-22/R-152a (1.5/87.5/11) | | |
| R-411B | R-1270/R-22/R-152a (3/94/3) | | |
| R-412A | R-22/R-218/R-142b (70/5/25) | | |
| R-413A | R-218/R-134a/R-600a (9/88/3) | | |
| R-414A | R-22/R-124/R-600a/R-142b (51/28.5/4.0/16.5) | | |
| R-414B | R-22/R-124/R-600a/R-142b (50/39/1.5/9.5) | | |
| R-415A | R-22/R-152a (82/18) | | |
| R-415B | R-22/R-152a (25/75) | | |
| R-416A | R-134a/R-124/R-600 (59/39.5/1.5) | | |
| R-417A | R-125/R-134a/R-600 (46.6/50.0/3.4) | | |
| R-418A | R-290/R-22/R-152a (1.5/96/2.5) | | |
| R-419A | R-125/R-134a/R-E170 (77/19/4) | | |
| R-420A | R-134a/R-142b (88/12) | | |
| R-421A | R-125/R-134a (58/42) | | |
| R-421B | R-125/R-134a (85/15) | | |
| R-422A | R-125/R-134a/R-600a (85.1/11.5/3.4) | | |
| R-422B | R-125/R-134a/R-600a (55/42/3) | | |
| R-422C | R-125/R-134a/R-600a (82/15/3) | | |
| R-422D | R-125/R-134a/R-600a (65.1/31.5/3.4) | | |
| R-423A | R-134a/R-227ea (52.5/47.5) | | |
| R-424A | R-125/R-134a/R-600a/R-600/R-601a (50.5/47/.9/1/.6) | | |
| R-425A | R-32/R-134a/R-227ea (18.5/69.5/12) | | |
| R-426A | R-125/R-134a/R-600/R-601a (5.1/93/1.3/.6) | | |
| R-427A | R-32/R-125/R-143a/R-134a (15/25/10/50) | | |
| R-428A | R-125/R-143a/R-290/R-600a (77.5/20/.6/1.9) | | |
| R-500 | R-12/R-152a (73.8/26.2) | | |
| R-501 | R-22/R-12 (75/25) | | |
| R-502 | R-22/R-115 (48.8/51.2) | | |
| R-503 | R-23/R-13 (40.1/59.9) | | |
| R-504 | R-32/R-115 (48.2/51.8) | | |
| R-505 | R-12/R-31 (78/22) | | |
| R-506 | R-31/R-114 (55.1/44.9) | | |
| R-507A | R-125/R-143a (50/50) | | |
| R-508A | R-23/R-116 (39/61) | | |
| R-508B | R-23/R-116 (46/54) | | |
| R-509A | R-22/R-218 (44/56) | | |
| R-600 | Butane | CH3CH2CH2CH3 | 106-97-8 |
| R-600a | Isobutane | CH(CH3)2CH3 | 75-28-5 |
| R-601 | Pentane | CH3CH2CH2CH2CH3 | 109-66-0 |
| R-601a | Isopentane | (CH3)2CHCH2CH3 | 78-78-4 |
| R-610 | Diethyl ether | C2H5OC2H5 | 60-29-7 |
| R-611 | Methyl formate | C2H4O | 107-31-3 |
| R-630 | Methylamine | CH2NH2 | 74-89-5 |
| R-631 | Ethylamine | C2H5NH2 | 75-04-7 |

TABLE 2-continued

| Designation | Name | Formula | CAS number |
|---|---|---|---|
| R-702 | Hydrogen | H2 | 1333-74-0 |
| R-704 | Helium | He | 7440-59-7 |
| R-717 | Ammonia | NH3 | 7664-41-7 |
| R-718 | Water | H2O | 7732-18-5 |
| R-720 | Neon | Ne | 7440-01-9 |
| R-728 | Nitrogen | N2 | 7727-37-9 |
| R-732 | Oxygen | O2 | 7782-44-7 |
| R-740 | Argon | Ar | 7440-37-1 |
| R-744 | Carbon dioxide | CO2 | 124-38-9 |
| R-744A | Nitrous oxide | N2O | 10024-97-2 |
| R-764 | Sulfur dioxide | SO2 | 7446-09-5 |
| R-784 | Krypton | Kr | 7439-90-9 |
| R-1112a | 1,1-Dichloro-2,2-difluoroethylene | C2Cl2F2 | 79-35-6 |
| R-1113 | Chlorotrifluoroethylene | C2ClF3 | 79-38-9 |
| R-1114 | Tetrafluoroethylene | C2F4 | 116-14-3 |
| R-1120 | Trichloroethylene | C2HCl3 | 79-01-6 |
| R-1130 | cis-1,2-Dichloroethylene | C2H2Cl2 | 156-59-2 |
| R-1132 | 1,1-Difluoroethylene | C2H2F2 | 75-38-7 |
| R-1140 | Chloroethylene | C2H3Cl | 75-01-4 |
| R-1141 | Fluoroethylene | C2H3F | 75-02-5 |
| R-1150 | Ethylene | C2H4 | 74-85-1 |
| R-1216 | Hexafluoropropene | C3F6 | 116-15-4 |
| R- | Hexafluoropropene trimer | (C3F6)3 | 6792-31-0 |
| R-1270 | Propylene | C3H6 | 115-07-1 |

Aspects of the subject matter described herein can be embodied in systems, apparatus, methods, and/or articles depending on the desired configuration. In particular, various aspects of the subject matter described herein can be realized in digital electronic circuitry, integrated circuitry, specially designed application specific integrated circuits (ASICs), computer hardware, firmware, software, and/or combinations thereof.

These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, programmable logic devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Although a few variations have been described in detail above, other modifications, additions, and implementations are possible are within the scope and spirit of the disclosed subject matter. Features implementing functions can also be physically located at various positions, including being distributed such that portions of functions are implemented at different physical locations. Further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein do not require the particular order shown, or sequential order, to achieve desirable results. Other embodiments may be within the scope of the following claims.

What is claimed is:

1. A method comprising:
    directing a beam of light at a selected wavelength through a gas mixture comprising water vapor and a background that comprises a plurality of refrigerant compounds, the water vapor having a water vapor concentration that is substantially lower than that a refrigerant concentration of the refrigerant compounds, the selected wavelength coinciding with a water vapor absorption feature that is resolvable from an absorption background resulting from absorption of light by the plurality of refrigerant compounds at the refrigerant concentration;
    quantifying an absorption of the beam of light at the selected wavelength in the gas mixture over a path length;
    determining the water vapor concentration in the gas mixture based on the quantified absorption; and
    promoting the determined water vapor concentration.

2. A method as in claim 1, wherein the promoting comprises one or more of displaying, transmitting, or storing the determined water vapor concentration.

3. A method as in claim 2, further comprising:
    generating light with a range of wavelengths, the range of wavelengths comprising the selected wavelength;
    tuning the generated light across the range of wavelengths; and
    converting a signal from a photodetector that the light beam impinges upon after traversing the gas mixture to an absorption spectroscopy signal by demodulating the signal; and
    analyzing the absorption spectroscopy signal to determine the water vapor concentration.

4. A method as in claim 3, wherein the quantifying of the absorption at the selected wavelength is accomplished using one of direct absorption spectroscopy, harmonic spectroscopy; photoacoustic spectroscopy, cavity ringdown spectroscopy, integrated cavity spectroscopy, and cavity enhanced spectroscopy.

5. A method as in claim 1, wherein the gas mixture is contained within a sample cell that provides the path length.

6. A method as in claim 1, wherein the absorption at the selected wavelength is quantified with a photodetector that provides a detector output signal to a microprocessor.

7. A method as in claim 1, wherein the water vapor concentration is less than or equal to approximately 1 ppm.

8. A method as in claim 1, wherein the water vapor concentration is less than or equal to approximately 0.1%.

9. A method as in claim 1, wherein the selected wavelength corresponds to a water absorption line at or adjacent to a wavelength selected from a group comprising: 1359.5 nm, 1361.7 nm, 1368.6 nm, 1371.0 nm, 1392.0 nm, 1836.3 nm, 1840.0 nm, 1842.1 nm, 1847.1 nm, 1854.0 nm, 1856.7 nm, 1859.8 nm, 1903.0 nm, 1905.4 nm, 2573.6 nm, 2583.9 nm, 2596.0 nm, 2605.6 nm, 2620.5 nm, 2626.7 nm, 2630.6 nm, 2665.1 nm, 2676.0 nm, 2711.2 nm, 2724.2 nm, 2735.0 nm, and 2740.0 nm.

10. A method as in claim 1, wherein the selected wavelength is chosen such that absorption of 1 ppmv of water vapor at the selected wavelength and a measurement pressure divided by a total background absorption of the plurality of refrigerant compounds in the gas mixture at the selected wavelength and the measurement pressure is greater than $1\times10-6$.

11. A method as in claim 1, further comprising providing the beam of light from a tunable diode laser that is tuned to provide a range of wavelengths comprising the selected wavelength.

12. A method as in claim 1, further comprising maintaining the gas mixture and the photodetector at a constant temperature within a tolerance of approximately $\pm 1°$ C.

13. A method as in claim 1, wherein the plurality of refrigerant compounds comprises a hydrofluorocarbon.

14. A method as in claim 13, wherein the hydrofluorocarbon is selected from a group comprising: HFC-134A, HFC-152A, HFC-23, HFC-32, HFC-143A, HFC-125, HFC-245FA, and HFC-227EA.

15. A method as in claim 1, wherein the selected wavelength corresponds to a water absorption line at or adjacent to a wavelength selected from a group comprising: 1877.1 nm, 1890.3 nm, and 1899.7 nm.

16. An apparatus comprising:
a laser light source that emits a light beam comprising a selected wavelength that coincides with a water vapor absorption feature that is resolvable from an absorption background resulting from absorption of light by a plurality of refrigerant compounds present at a refrigerant concentration in a gas mixture when a water vapor concentration is substantially lower than that a refrigerant concentration of the refrigerant compounds;
a sample cell to contain the gas mixture containing water vapor at a concentration of less than or equal to approximately 0.1%, the sample cell providing a path length of 1 cm or more for the light beam through the refrigerant gas;
a photodetector positioned to quantify an intensity of light traversing the path length and to output a signal based on the quantified intensity; and
a microprocessor configured to receive and interpret the signal from the photodetector and to determine the water vapor concentration in the gas mixture based on the data signal.

17. An apparatus as in claim 16, wherein the selected wavelength corresponds to a water absorption line at or adjacent to a wavelength selected from a group comprising: 1359.5 nm, 1361.7 nm, 1368.6 nm, 1371.0 nm, 1392.0 nm, 1836.3 nm, 1840.0 nm, 1842.1 nm, 1847.1 nm, 1854.0 nm, 1856.7 nm, 1859.8 nm, 1903.0 nm, 1905.4 nm, 2573.6 nm, 2583.9 nm, 2596.0 nm, 2605.6 nm, 2620.5 nm, 2626.7 nm, 2630.6 nm, 2665.1 nm, 2676.0 nm, 2711.2 nm, 2724.2 nm, 2735.0 nm, and 2740.0 nm.

18. An apparatus as in claim 16, wherein the selected wavelength is chosen such that absorption of 1 ppmv of water vapor or more at the selected wavelength and a measurement pressure divided by a total background absorption of the gas mixture at the selected wavelength and the measurement pressure is equal to or greater than $1\times10-6$.

19. An apparatus as in claim 16, wherein the laser light source is a tunable diode laser that emits light within a wavelength range that comprises the selected wavelength.

20. An apparatus as in claim 19, wherein the laser light source is modulated based on a modulation signal provided by the microprocessor and wherein the microprocessor is configured to demodulate the direct current signal from the photodetector to generate an absorption spectroscopy signal that is analyzed to determine the intensity of light traversing the path length at the selected wavelength.

21. An apparatus as in claim 19, wherein the laser light source is selected from a vertical cavity surface emitting laser, a horizontal cavity surface emitting laser, a quantum cascade laser, a distributed feedback laser, or a color center laser.

22. An apparatus as in claim 16, further comprising a thermally monitored or controlled chamber that encloses one or more of the laser source, the photodetector, and the sample cell.

23. An apparatus as in claim 16, wherein the sample cell comprises at least two reflective mirrors configured to reflect the light beam between them one or more times before the light beam reaches the photodetector.

24. A method comprising:
generating a beam of light comprising a selected wavelength from a tunable laser, the selected wavelength being selected such that absorption of 1 ppmv of water vapor at the selected wavelength divided by absorption by a plurality of refrigerant compounds present at a refrigerant concentration in a gas mixture at the selected wavelength is greater than $1\times10^{-6}$;
directing the beam of light through a refrigerant gas comprising water vapor at a concentration of less than or equal to approximately 0.1%;
quantifying an absorption of the beam of light at the selected wavelength in the gas mixture over a path length and at a pressure of approximately 1 atmosphere;
determining a water vapor concentration in the gas mixture based on the quantified absorption; and
promoting the determined water vapor concentration.

25. A method as in claim 24, further comprising providing the beam of light from a tunable diode laser that is tuned to provide a range of wavelengths comprising the selected wavelength.

* * * * *